United States Patent
Goldfine et al.

(10) Patent No.: US 7,161,351 B2
(45) Date of Patent: Jan. 9, 2007

(54) HIDDEN FEATURE CHARACTERIZATION USING A DATABASE OF SENSOR RESPONSES

(75) Inventors: Neil J. Goldfine, Newton, MA (US); Vladimir A. Zilberstein, Chestnut Hill, MA (US); Darrell E. Schlicker, Watertown, MA (US); David C. Grundy, Reading, MA (US); Ian C. Shay, Waltham, MA (US); Robert J. Lyons, Boston, MA (US); Andrew P. Washabaugh, Chula Vista, CA (US)

(73) Assignee: Jentek Sensors, Inc., Waltham, MA (US)

( * ) Notice: Subject to any disclaimer, the term of this patent is extended or adjusted under 35 U.S.C. 154(b) by 177 days.

(21) Appl. No.: 10/934,103

(22) Filed: Sep. 3, 2004

(65) Prior Publication Data

US 2005/0088172 A1    Apr. 28, 2005

Related U.S. Application Data

(60) Provisional application No. 60/500,040, filed on Sep. 3, 2003, provisional application No. 60/591,662, filed on Jul. 27, 2004.

(51) Int. Cl.
   *G01R 33/12* (2006.01)
(52) U.S. Cl. .................. 324/242; 324/240; 324/226; 228/102
(58) Field of Classification Search .............. 324/240, 324/242, 243, 236–238, 228–233, 226; 228/102–104
   See application file for complete search history.

(56) References Cited

U.S. PATENT DOCUMENTS

| | | | |
|---|---|---|---|
| 4,814,690 A | 3/1989 | Melcher et al. | |
| 5,015,951 A | 5/1991 | Melcher | |
| 5,453,689 A | 9/1995 | Goldfine et al. | |
| 5,793,206 A | 8/1998 | Goldfine et al. | |
| RE36,986 E | 12/2000 | Melcher | |
| 6,188,218 B1 | 2/2001 | Goldfine et al. | |
| 6,377,039 B1 | 4/2002 | Goldfine et al. | |
| 6,380,747 B1 | 4/2002 | Goldfine et al. | |
| 6,486,673 B1 | 11/2002 | Goldfine et al. | |
| 6,657,429 B1 | 12/2003 | Goldfine et al. | |
| 6,727,691 B1 * | 4/2004 | Goldfine et al. | ............ 324/240 |
| 6,781,387 B1 | 8/2004 | Goldfine et al. | |
| 2002/0075006 A1 | 6/2002 | Goldfine et al. | |
| 2002/0163333 A1 | 11/2002 | Schlicker et al. | |
| 2003/0071615 A1 | 4/2003 | Schlicker et al. | |
| 2004/0021461 A1 | 2/2004 | Goldfine et al. | |
| 2004/0056654 A1 | 3/2004 | Goldfine et al. | |
| 2005/0007106 A1 | 1/2005 | Goldfine et al. | |

OTHER PUBLICATIONS

ASTM Standard E2338-04.

(Continued)

*Primary Examiner*—Jay M. Patidar
(74) *Attorney, Agent, or Firm*—Hamilton, Brook, Smith & Reynolds, P.C.

(57) ABSTRACT

Quasistatic sensor responses may be converted into multiple model parameters to characterize hidden properties of a material. Methods of conversion use databases of responses and, in some cases, databases that include derivatives of the responses, to estimate at least three unknown model parameters, such as the electrical conductivity, magnetic permeability, dielectric permittivity, thermal conductivity, and/or layer thickness. These parameter responses are then used to obtain a quantitative estimate of a property of a hidden feature, such as corrosion loss layer thicknesses, inclusion size and depth, or stress variation. The sensors can be single element sensors or sensor arrays and impose an interrogation electric, magnetic, or thermal field.

29 Claims, 17 Drawing Sheets

OTHER PUBLICATIONS

Haus, H.A. and Melcher, J.R. (1989), "Electromagnetic Fields and Energy," Prentice-Hall Inc., Englewood Cliffs, NJ.

Air Force Phase II Final Report, titled "Detection and Imaging of Inclusions and Planar Flaws in Titanium Castings Including Weld Repaired Regions," Topic #AF00-162, dated Apr. 8, 2003.

Technical paper titled "Enhancements in MWM-Array Hidden Corrosion Imaging," JENTEK docket No. TP_2003_0801.

Technical presentation titled "High-Resolution Residual Stress Imaging Using MWM-Arrays with Pre-Computed Response Databases," QNDE Conference, Colorado School of Mines, Jul. 2004.

* cited by examiner

HIDDEN FEATURE CHARACTERIZATION USING A DATABASE OF SENSOR RESPONSES

RELATED APPLICATIONS

This application claims the benefit of U.S. Provisional Application No. 60/500,040, filed on Sep. 3, 2003, and of U.S. Provisional Application No. 60/591,662 filed on Jul. 27, 2004. The entire teachings of the above applications are incorporated herein by reference.

BACKGROUND OF THE INVENTION

The aspects of this invention deal with nondestructive materials characterization, particularly as it applies to the rapid and quantitative model-based characterization of hidden features. Examples of materials characterization include assessment of material loss from corrosion, characterization of hidden geometries such as the size, depth, and presence of defects around cooling holes or sealant grooves, and the detection and assessment of size and depth for buried inclusions. A common technique suitable for these inspections involves eddy current sensing.

Conventional eddy-current sensing involves an excitation of a conducting winding, the primary, with an electric current source of prescribed frequency. This produces a time-varying magnetic field, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks.

In many inspection applications, large surface areas of a material need to be tested, such as a lap joint of an aircraft. This inspection can be accomplished with a single sensor and a two-dimensional scanner over the material surface. However, the use of a single sensor has disadvantages in that the scanning can take an excessively long time and care must be taken when registering the measured values together to form a map or image of the properties. These shortcomings can be overcome by using an array of sensors, but each sensor must be driven sequentially in order to prevent cross-talk or cross-contamination between the sensors. Alternatively, multiple sense elements can be used with a single drive winding. With known positions between each array element, the material can be scanned in a shorter period of time and the measured responses from each array element are spatially correlated.

Furthermore, detection of damage is often insufficient by itself and more quantitative or detailed assessments are required to determine the appropriate course of action. For example, prediction of corrosion fatigue life is still difficult, but limited information about the shape and nature of corrosion damage can provide useful information for prioritization of dealing with detected corrosion damage. Decision support for maintenance and repair for individual aircraft, as well as for depot and fleetwide initiatives, requires such information.

In another application of materials characterization, the structural integrity of titanium castings used to achieve significant cost savings during the manufacture of complex aircraft structural components depends largely on the capability of non-destructive inspection (NDI) methods to detect detrimental flaws. The primary defects found in titanium castings are voids or local porosity, cracks and inclusions. Inclusions can originate from contamination during manufacturing processes or from the shell material from investment casting molds. A specific type of deleterious inclusion of particular importance for titanium alloy component integrity is hard alpha inclusions in titanium castings. Hard alpha inclusions are particularly harmful when they reside in the near-surface region, where they are more likely to serve as initiation sites for fatigue cracks in cyclically loaded structures.

Considerable effort has been invested in NDI for titanium castings. Porosity, cracks and high-density inclusions (i.e., tungsten) in castings are not usually considered a problem because they are controlled by specifications and standard NDI sensitivity. The detection of shell inclusions and some types of alpha-stabilized nuggets presents a more difficult detection problem. X-ray sensitivity to these features is poor, to the point of non-detectability at material thickness of 0.75 in. (19 mm) or greater in many cases. Phased array ultrasonic testing (UT) has become the method of choice for detection of inclusions, but suffers from what is considered a dead zone (poor sensitivity) in the first 0.06 in. (1.5 mm) of the surface. In the areas where immersion scanning cannot be performed, the near-surface dead zone is roughly 0.15 in. (3.8 mm) using contact phased array inspection. Scanning from the opposite side of the part, if possible, is currently the only way to cover such dead zones. Electromagnetic inspection of the near-surface region of titanium typically looks for variations in material conductivity, where the hard alpha and other inclusions possess a different conductivity relative to the surrounding titanium matrix.

SUMMARY OF THE INVENTION

Aspects of the methods described herein involve novel methods and apparatus for measurement of the near surface hidden properties of conducting and/or magnetic materials. These methods use sensors and arrays that can be accurately modeled so that the sensor responses can readily be converted into at least three model parameters. In turn, one or more of the model parameters are then related to the properties of the material feature of interest, either directly or indirectly, through a predetermined correlation.

One embodiment of the invention involves disposing a sensor proximate to the test material and exciting the sensor in a quasistatic regime. This typically involves operating the sensor at a sufficiently low excitation frequency that diffusion and laplacian decay of the interrogating fields into the test material dominate the wave effects of the fields. In various embodiments, the sensor or sensor arrays can use electric, magnetic, or thermal fields, depending upon the electrical geometric, and thermal properties of the test materials. Furthermore, the model is used to create a pre-computed database of responses prior to data acquisition so that after the measurement data only needs to be converted into model parameters after being acquired. At least three model parameters are being determined as part of this conversion, with three or four parameters preferred. In various embodiments of the invention, an estimated parameter may be an electrical conductivity, a magnetic permeability, a lift-off, or a layer thickness. In an embodiment, the database may also include the derivatives of the response variations with respect to the model parameters in order to reduce the processing time for converting the measurement data into parameter estimates.

In one embodiment of the invention, the sensor has separate drive and sense electrodes, where the drive imposes the interrogating field. This interrogating field is perturbed by the properties of the test material and resulting fields is monitored with the sense electrodes. The sense electrodes can be configured as an array of elements. In one embodiment of the invention, at least one of the sense elements is at a different distance to the drive than the other sense elements so that multiple field penetration depths into the test material are being monitored.

In one embodiment of the invention, the feature of interest is a loss of material from corrosion. In alternative embodiments of the invention, the corresponding properties of interest may be the thickness of a material layer or the remaining material thickness if more than one layer is present. In one embodiment of the invention, the test material is a lap joint having at least two material or metal layers. Properties of interest may then include a gap between the two layers as well as the thickness of each material layer. In an alternative embodiment of the invention, the model may include a thickness of any protective coatings that can influence the sensor response.

In another embodiment of the invention, the feature of interest is an inclusion or local porosity in the test material. Properties of interest may then include the size, shape, and depth of the inclusion. Another hidden feature may be a sealant groove, located at the hidden interface with another material, or a cooling hole in a turbine blade. In yet another embodiment of the invention, the hidden property of interest may be a mechanical stress variation, either in the bulk or at a material interface. The property may be hidden because of an overlay coating, which is accounted for in the model of the responses. In one embodiment of the invention, the model accounts for a nonmagnetic conducting material layer on a magnetic layer where the stress dependent magnetic permeability is monitored by the sensor.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The use of sensors or sensors arrays with databases created from physical or numerical models that accurately predict the sensor response permits rapid quantitative characterization of hidden features. The type of sensor being used may depend upon the properties of the test material and the nature of the feature. For example, for conducting and/or magnetic materials, magnetic field based eddy current sensors or magnetometers may be used. For insulating or relatively poor conductors, electric field based dielectrometers or capacitive sensors may be used. For delaminations in composites, thermal sensors may be used. In each case, the sensor is operated in a quasistatic regime where the temporal excitation frequency is low enough so that the interrogating field (such as the magnetic, electric, or thermal) in the proximity of the sensor is not described by a simple wave equation and the model accounts for the laplacian or diffusion decay of the field into the test material. Measurement data is combined with the model response to simultaneously estimate the values for multiple model parameters, which are then correlated to the properties of the feature or features of interest.

Figure 1:
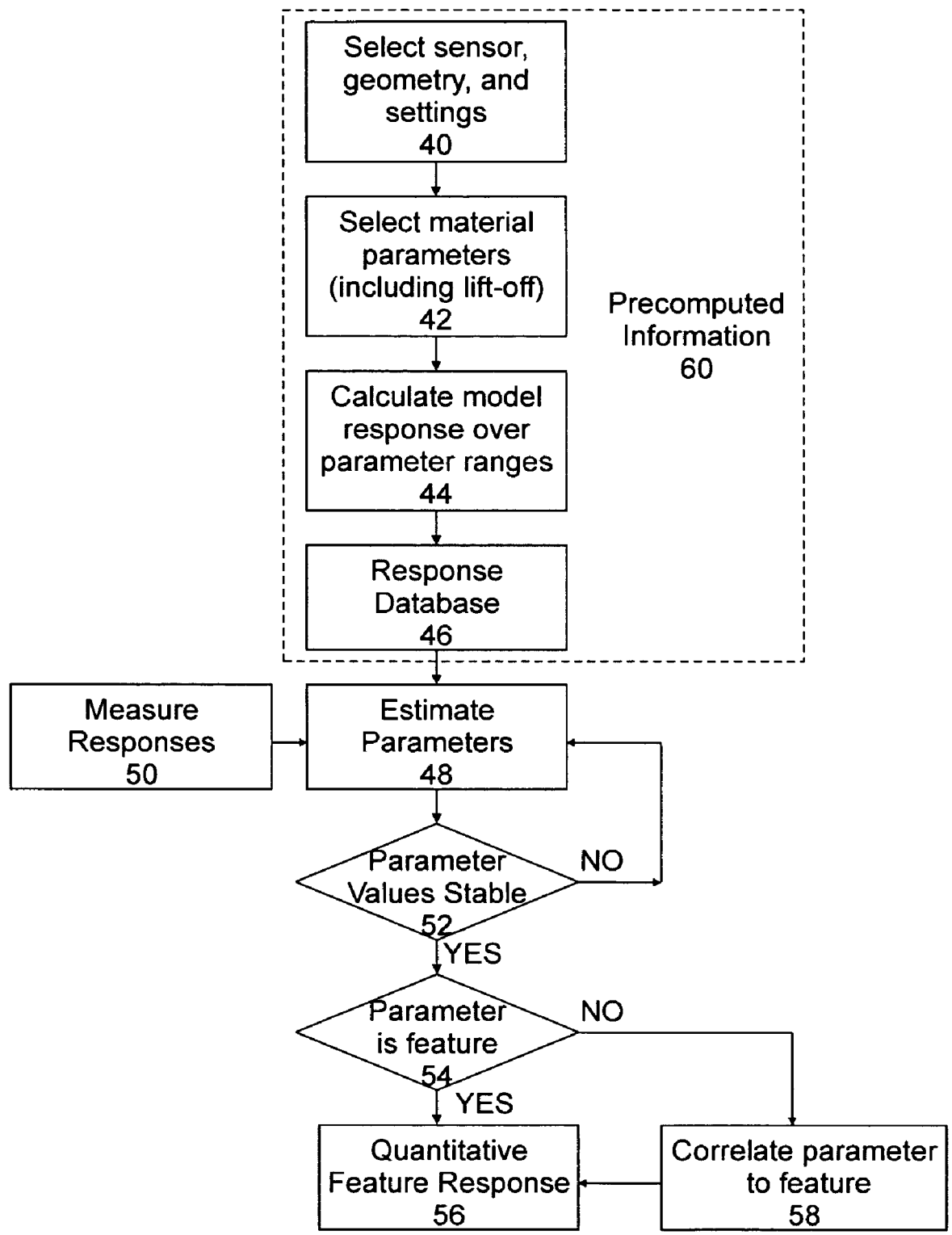
FIG. 1 is a flow chart for the method for converting measurement data into feature properties.

FIG. 1 illustrates this approach to detecting hidden features. Precomputed information 60 is used prior to acquisition of data or measurement responses 50 to facilitate converting the measurement data into quantitative estimates of the feature values. Prior to data acquisition, settings 40 for the sensor type, geometry, and measurement are selected. This involves selecting a sensor type (e.g., magnetic, electric, or thermal), a geometry for any drive and sense elements, and material properties associated with these elements and any support materials. Any instrumentation parameters, such as the excitation frequency, for the measurement may also be selected. A model is then set for representing the test material 42. For layered materials, this selection typically involves choosing the physical properties (magnetic permeability, electrical conductivity, dielectric permittivity, and/or thermal conductivity) and the geometric properties (thicknesses) for each of the layers. Note that the sensor proximity or lift-off is typically modeled as an insulating layer where the thickness is an unknown parameter.

This step also requires setting ranges for the parameters to be determined. These parameters are the unknown properties to be determined by the measurement. They can directly reflect the feature property of interest, such as the thickness of a layer, or they may be correlated to a feature property of interest, such as the electrical conductivity reflecting the porosity of a material layer. This information is then used to calculate the model response 44 that goes into a database of responses 46 that can be accessed during data acquisition.

During data acquisition, or soon thereafter for near real-time measurements, the measured response data 50 is combined with the response databases 46 to estimate the unknown model parameters 48. This estimation can take the form of direct inversion of the data using interpolation method or indirect methods that minimize the difference between the model and measured responses using, for example, least-squares, root-searching, simplex, modified simplex, or conjugate gradient techniques. For two dimensional databases, where there are only two unknown parameters, direct inversion techniques may be applied as described later. However, one embodiment of this invention is concerned with the estimation of the three or more parameters from the measurement data. Note also that to increase the speed of the estimation, the response database may also include derivatives or rates of change of the model responses with respect to the unknown parameter values. This is basically a Jacobian for the sensor responses and has been described for example in U.S. Pat. No. 5,453,689, the entire teachings of which are incorporated herein by reference.

After estimating the parameter values, the stability of the estimated values should be checked (52). This can involve, for example in the case of the simplex routine, perturbing the estimated responses and re-estimating the values to determine if they approach the same values as before. If not, then estimate routine needs to be modified, such as starting at different initial values, to get convergence at stable values. Once stable or robust parameter estimates are obtained, then the next check 54 is to determine if a parameter or a combination of the parameters then provides a quantitative estimate of the feature property of interest 56. Otherwise, a correlation between the estimated parameter or a combination of the estimated parameters 58 is then used to obtain the quantitative estimate of the feature property or properties.

One of the key features of this approach is to use sensors in a quasistatic regime where the response of the sensor proximate to a test material can be modeled accurately using physical or numerical methods. This implies that the interrogating fields near the sensor and the source distribution for these fields are being modeled self-consistently. In contrast, models that simply rely on the wave equation for the propagation (and decay) of the interrogating fields into the test material typically assume a known source distribution. For electromagnetic sensors, the quasistatic response typically requires operation at a low enough frequency that electromagnetic wave response is not appreciable. The critical frequency for having to consider wave dynamics depends upon the length scales or geometry under consideration, as well as the physical properties of the material, as described for example in Haus and Melcher. For most near-field sensing applications, this typically translates to a measurement frequency of less than 100 MHz. Without a significant wave response, this also allows the decoupling of the temporal and spatial modes for the fields. For example, this was phrased as an "omega-k" approach in U.S. Pat. Nos. 5,015,951 and Re. 36,986, the entire teachings of which are incorporated herein by reference, where "omega" refers to the angular temporal excitation frequency and "k" refers to the spatial wavenumber, and permits interrogation of a material to multiple depths at the same excitation frequency.

Figure 2:
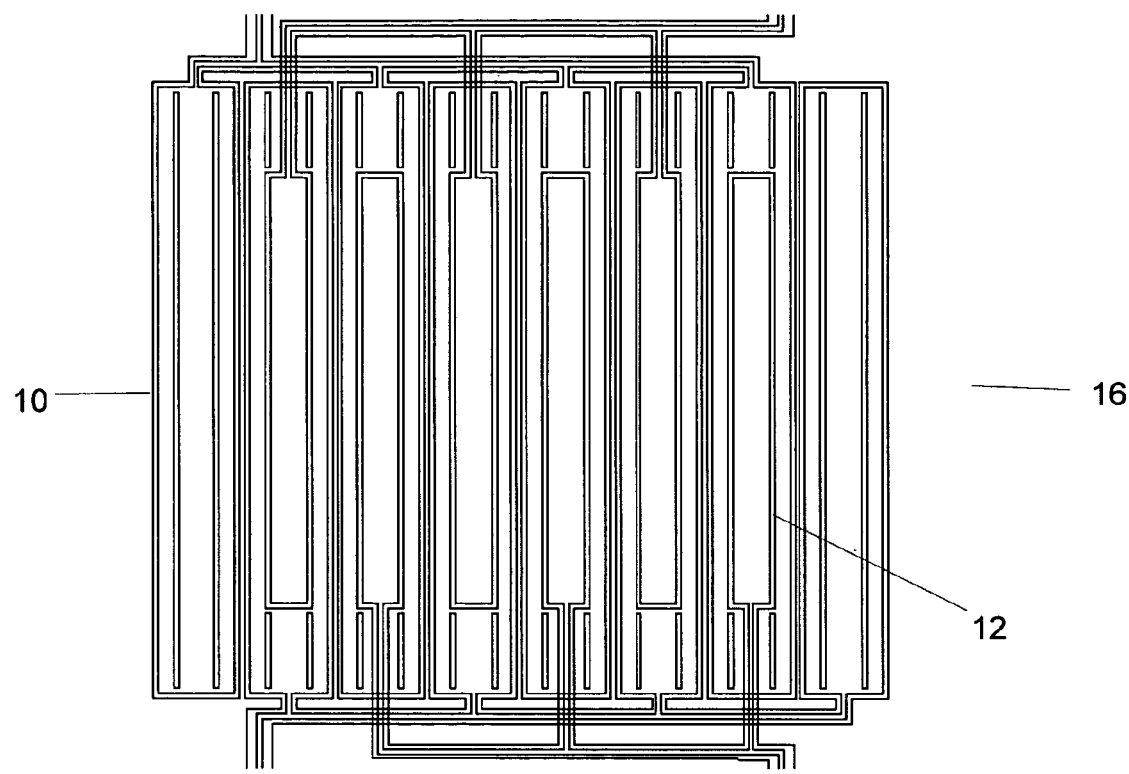
FIG. 2 illustrates a plan view for an MWM sensor.

An example suitable magnetic field base eddy current sensor is shown in FIG. 2. This figure illustrates the basic geometry of an MWM® sensor 16, a detailed description of which is given in U.S. Pat. Nos. 5,453,689, 5,793,206, and 6,188,218 and U.S. patent application Ser. Nos. 09/666,879 and 09/666,524, both filed on Sep. 20, 2000, the entire teachings of which are incorporated herein by reference. The sensor includes a primary winding 10 having extended portions for creating the magnetic field and secondary windings 12 within the primary winding for sensing the response. The primary winding is fabricated in a spatially periodic pattern with the dimension of the spatial periodicity termed the spatial wavelength λ. A current is applied to the primary winding to create a magnetic field and the response of the material under test (MUT) to the magnetic field is determined through the voltage measured at the terminals of the secondary windings. This geometry creates a magnetic field distribution similar to that of a single meandering winding. A single element sensor has all of the sensing elements connected together. The magnetic vector potential produced by the current in the primary can be accurately modeled as a Fourier series summation of spatial sinusoids, with the dominant mode having the spatial wavelength $\lambda$. For an MWM-Array, the responses from individual or combinations of the secondary windings can be used to provide a plurality of sense signals for a single primary winding construct as described in U.S. Pat. Nos. 5,793,206 and Re. 36,986.

The MWM is a "planar," conformable eddy-current sensor that was designed to support quantitative and autonomous data interpretation methods. These methods, called grid measurement methods, permit crack detection on curved surfaces without the use of crack standards, and provide quantitative images of absolute electrical properties (conductivity and permeability) and coating thickness without requiring field reference standards (i.e., calibration is performed in "air," away from conducting surfaces). MWM sensors and MWM-Arrays can be used for a number of applications, including fatigue monitoring and inspection of structural components for detection of flaws, degradation and microstructural variations as well as for characterization of coatings and process-induced surface layers. Characteristics of these sensors and sensor arrays include directional multi-frequency magnetic permeability or electrical conductivity measurements over a wide range of frequencies, e.g., from 250 Hz to 40 MHz with the same MWM sensor or MWM-Array, high-resolution imaging of measured permeability or conductivity, rapid permeability or conductivity measurements with or without a contact with the surface, and a measurement capability on complex surfaces with a hand-held probe or with an automated scanner. This allows the assessment of applied and residual stresses as well as permeability variations in a component introduced from processes such as grinding operations as described in U.S. patent application Ser. No. 10/441,976, filed May 20, 2003, the entire teachings of which are incorporated herein by reference.

Figure 3:
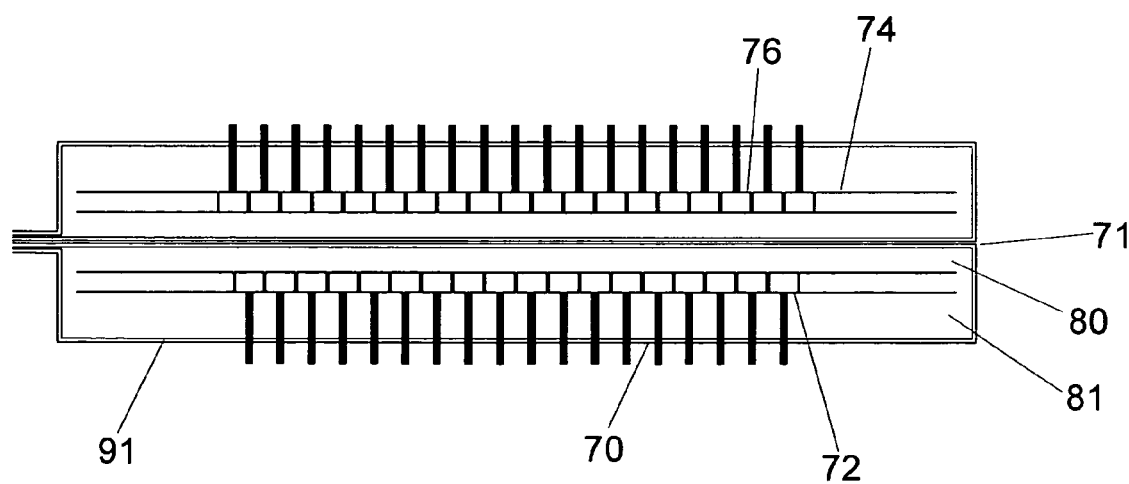
FIG. 3 is an expanded view of the drive winding and sense elements for an eddy-current array having offset rows of sensing elements.
Figure 4:
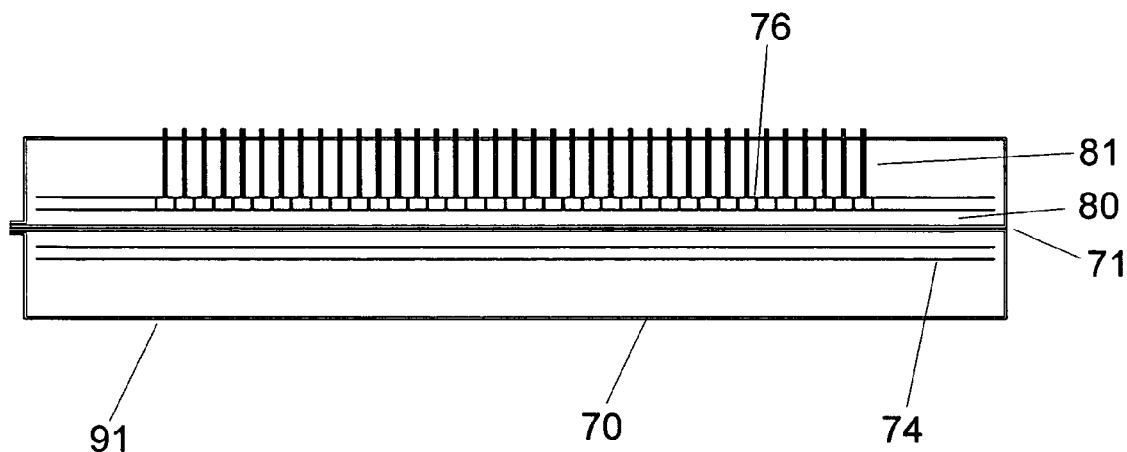
FIG. 4 is an expanded view of the drive winding and sense elements for an eddy-current array having a single row of sensing elements.

Example sensor arrays are shown in FIG. 3 through FIG. 7 some embodiments of which are described in detail in U.S. patent application Ser. Nos. 10/102,620, filed Mar. 19, 2002, Ser. No. 10/155,887, filed May 23, 2002, and 10/853,009, filed May 24, 2004, the entire teachings of which are incorporated herein by reference. These arrays include a wound coil primary winding 70 having extended portions for creating the magnetic field and a plurality of secondary elements 76 within the primary winding for sensing the response to the MUT. The secondary elements are pulled back from the connecting portions of the primary winding to minimize end effect coupling of the magnetic field. Dummy elements 74 can be placed between the meanders of the primary to maintain the symmetry of the magnetic field, as described in U.S. Pat. No. 6,188,218, the entire teachings of which are incorporated herein by reference. When the sensor is scanned or when a feature (or object) propagates across the sensor, perpendicular to the extended portions of the primary winding, secondary elements 72 in a primary winding loop adjacent to the first array of sense elements 76 provide a complementary measurement. Also, the sensor may be rotated or tilted relative to the object. These arrays of secondary elements 72 can be aligned with the first array of elements 76 so that images of the material properties will be duplicated by the second array. Note that improving the signal-to-noise through combining the responses or providing sensitivity on opposite sides of a feature such as a fastener is described in U.S. patent application Ser. Nos. 10/102,620 and 10/155,887. Alternatively, to provide complete coverage when the sensor is scanned across a part the sensing elements, can be offset along the length of the primary loop perpendicular to the extended portions of the primary winding, as illustrated in FIG. 3.

Figure 5:
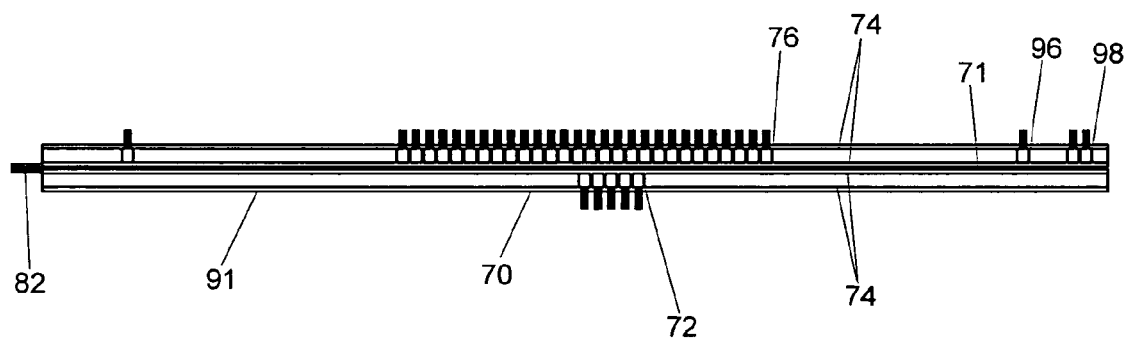
FIG. 5 is an expanded view of an eddy-current array where the locations of the sensing elements along the array are staggered.

The dimensions for the sensor array geometry and the placement of the sensing elements can be adjusted to improve sensitivity for a specific inspection. For example, the effective spatial wavelength or four times the distance 80 between the central windings 71 and the sensing elements 72 can be altered to adjust the sensitivity of a measurement for a particular inspection. For the sensor array of FIG. 3, the distance 80 between the secondary elements 72 and the central windings 71 is smaller than the distance 81 between the sensing elements 72 and the return windings 91. An optimum response can be determined with models, empirically, or with some combination of the two. An example of a modified sensor design is shown FIG. 4. In this sensor array, all of the sensing elements 76 are on one side of the central drive windings 71. The size of the sensing elements and the gap distance 80 to the central drive windings 71 are the same as in the sensor array of FIG. 2. However, the distance 81 to the return of the drive winding has been increased, as has the drive winding width to accommodate the additional elements in the single row of elements. Increasing the distance to the return reduces the size of the response when the return crosses a feature of interest such as a crack. Another example of a modified design is shown in FIG. 5. Here, most of the sensing elements 76 are located in a single row to provide the basic image of the material properties. A small number of sensing elements 72 are offset from this row to create a higher image resolution in a specific location. Other sensing elements are distant from the main grouping of sensing elements at the center of the drive windings to measure relatively distant material properties, such as the base material properties for plates at a lap joint or a weld or even the thickness of a cladding layer such as alclad that should be similar to the thickness of the cladding layer of a feature of interest, such as the gap between layers or layer thicknesses in a lap joint.

There is a tradeoff between the sensing element size and instrument that contributes to the achievable performance of such scanning measurements. A principal limitation of conventional eddy current methods is the low spatial resolution data produced by relatively large diameter eddy current coils. This large diameter for traditional eddy current coils is required to obtain a sufficient depth of penetration. The MWM-Array circumvents this problem by using an array, typically linear, of small sensing elements within a single large spatial wavelength drive, which provides the necessary penetration depth. Thus, both small sensing element size and deep field penetration can be provided at the same time. Small sensing elements can provide a relatively high spatial resolution data, suitable for accurate mapping of corrosion loss of hidden feature characterization. However, as the sensing element size is reduced, the inductive coupling to the secondary is also reduced, so that the corresponding signal-to-noise ration is correspondingly reduced. This is especially true at low frequencies where instrument noise and drift are often the most substantial noise sources. The signal magnitude on the secondary typically increases with increasing frequency, so using higher frequencies can help improve the signal-to-noise ratio. In general, the highest frequency appropriate for the application should be used, and then all efforts to reduce instrument and other noise should be attempted.

Figure 6:
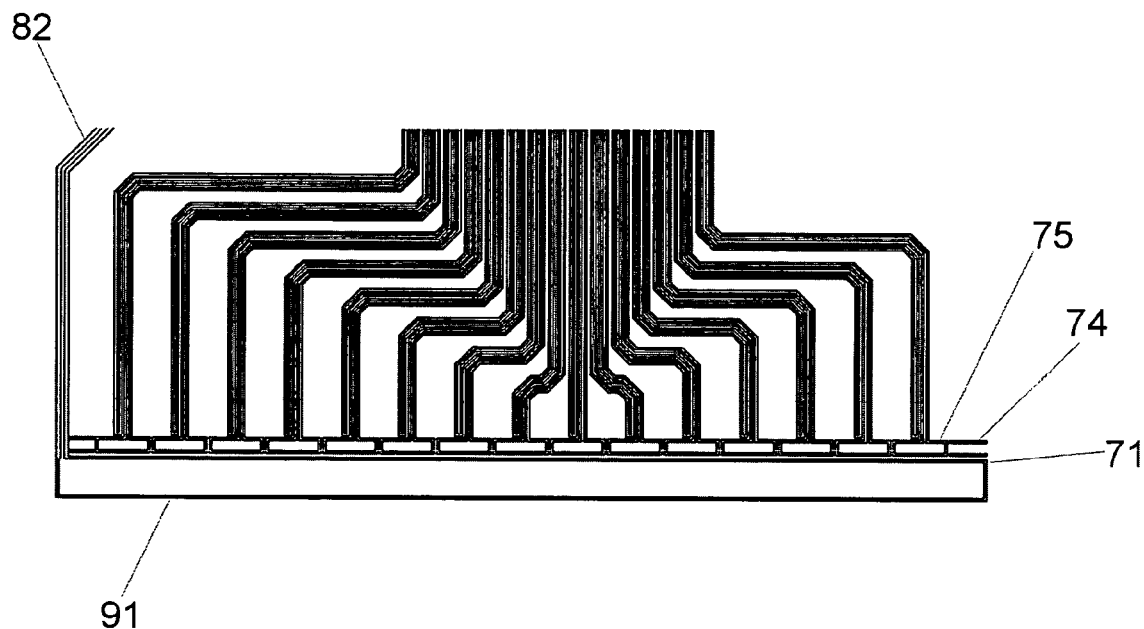
FIG. 6 is an expanded view of an eddy current array with a single rectangular loop drive winding and a linear row of sense elements on the outside of the extended portion of the loop.
Figure 7:
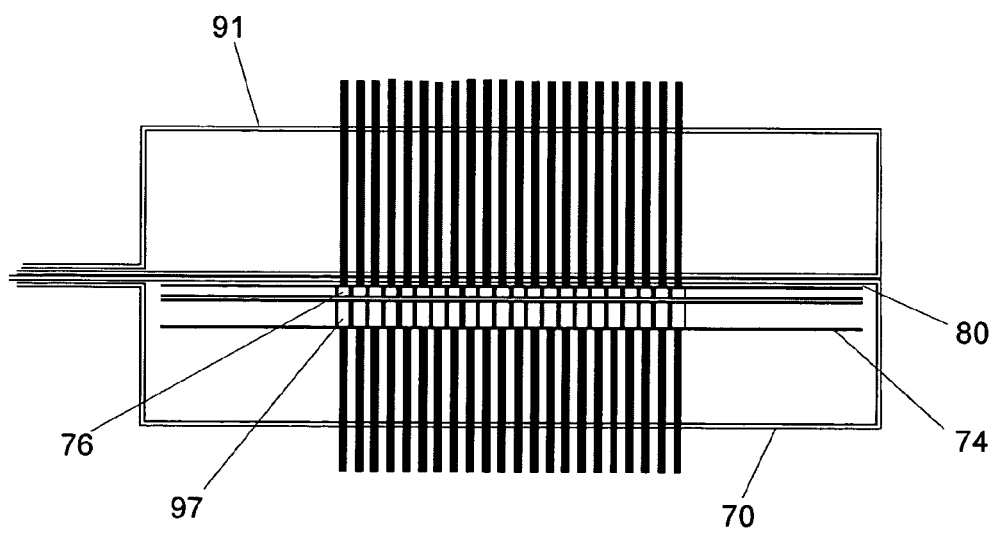
FIG. 7 is an expanded view of an eddy current array with a dual rectangular loop drive winding and two rows of sense elements at different distances to the drive winding.

The number of windings used in the primary winding can be reduced further so that a single rectangular drive is used. As shown in FIG. 6, a single winding loop having extended portions is used for the primary winding. A row of sensing elements 75 is placed on the outside of one of the extended portions. This is similar to designs described in U.S. Pat. No. 5,453,689 where the effective wavelength of the dominant spatial field mode is related to the spacing between the drive winding and sensing elements. This spacing can be varied to change the depth of sensitivity to properties and defects. This distance is optimized using models to maximize sensitivity to a feature of interest such as a buried crack or stress at a specific depth. Advantages of the design in FIG. 6 include a narrow drive and sense structure that allows measurements close to material edges and non-crossing winding pathways so that a single layer design can be used with all of the conductors in the sensing region in the same plane. Additional rows of sense elements can be placed on the opposite side of the drive 71 at the same or different distances from the drive. Sensing elements can be placed in different layers to provide multiple lift-offs at the same or different positions.

Sense elements can also be placed at different distances to the drive winding to sample different portions of the magnetic field in a segmented field manner. The sense elements further from the drive winding sample magnetic fields that tend to penetrate deeper into the test material so that sense elements at different distances to the drive winding sample different segments of the magnetic field. One example array, shown in FIG. 7 and described in U.S. patent application Ser. Nos. 10/155,887, filed on May 23, 2002, and 10/454,383, filed on the Jun. 3, 2003, the entire teachings of which are incorporated herein by reference, has a second array of sense elements 97 further from the central drive windings than the first array of sense elements 76. In this case, in order to make connections to the individual sense elements, the leads to the sense elements are in a different plane than the primary winding. Also in this case the elements 97 are larger than the elements 76 so that the both sets of elements would link the same amount of magnetic flux when the sensor array is in air as the magnetic field decays with distance from the primary winding windings. As a further alternative, other sensing elements such as giant magnetoresistive (GMR) devices that respond to the magnetic field could be used as the sense elements that are further away from the primary winding. These elements may provide more sensitivity to the field, particularly at low frequencies, than similar sized inductive coils, which respond to the time rate of change of the magnetic flux through the coil. In some cases, the combination of inductive coils near the primary winding and GMR sensors further away can provide the segmented field sensing capability with the greatest sensitivity to the magnetic field. Of course other types of one-dimensional or two-dimensional arrays of sense elements could also be used. This includes orienting one or more of the sense elements to be sensitive to other components of the magnetic field. Placing the sense elements at different distances to the drive windings also provides information about property variations with depth into the material, without changing the excitation frequency. This is particularly useful for materials having dispersive or frequency dependent effective properties where varying the frequency is not an effective method for changing the penetration depth of the magnetic field into the material, since the properties themselves are changing with the frequency.

One of the limitations of the use of inductive secondary coils in magnetometers is the depth of sensitivity to deep features. For a spatially periodic primary winding structure, the dimension of the spatial periodicity can be termed the spatial wavelength $\lambda$. The depth of penetration of the magnetic field into the MUT is then related to both $\lambda$ and the conventional skin depth; the penetration depth is limited to approximately $\lambda/6$ at low frequencies, and the skin depth at high frequencies. Thus, at low frequencies, increasing the wavelength increases the depth of penetration and allows the sensor to be sensitive to deeper features. However, the induced voltage on the secondary coils is proportional to the rate of change of the magnetic flux with time, or the excitation frequency, so that the frequency cannot be lowered indefinitely otherwise the signal is lost in measurement noise. To overcome these low-frequency limitations, alternative sensing elements based on solid-state device technology, such as GMR devices, Hall effect devices, and SQUIDS, can be used. In particular, sensing element arrays that use GMR sensors permit inspection measurements down to low frequencies, such as 50 Hz or even dc, for characterization of relatively thick plates, such as 0.5 inch aluminum-lithium alloy plates. Another technique for increasing the depth of penetration of an MWM-Array is to shape the magnetic field with the geometry of the primary winding. This allows for relatively long wavelength excitations with modest sensor footprints. The use of a GMR sensor as the sensing element in a magnetometer and the use of arrays of sensing elements and rectangular winding structures are described in U.S. patent application Ser. No. 10/045,650, submitted Nov. 8, 2001, the entire contents of which are hereby incorporated.

Figure 8:
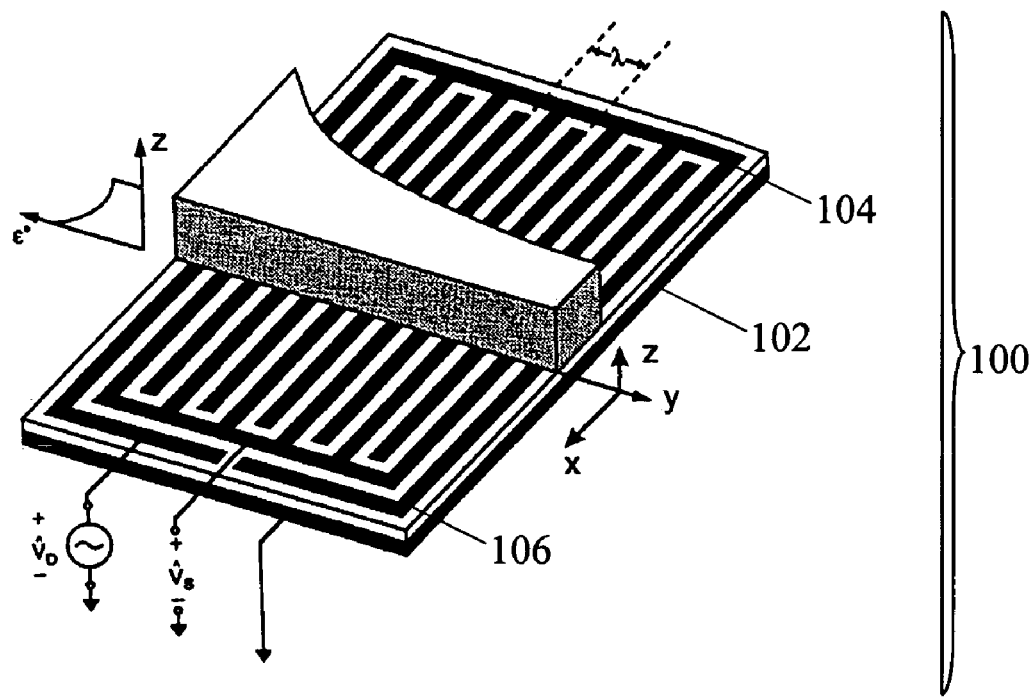
FIG. 8 is a representative single wavelength interdigitated electrode dielectrometer with spatially periodic driven and sensing electrodes of wavelength λ that can measure dielectric properties of the adjacent material.

For insulating or weakly conducting materials such as fiberglass composites, capacitive or dielectric sensors can be used. The sensors are the electromagnetic dual to the inductive sensors, with electric fields taking the place of magnetic fields for inspecting the materials. A representative single sided sensor geometry is shown in FIG. 8. The application of a sinusoidally varying potential of complex magnitude v and angular frequency $\omega=2\pi f$ results in the flow of a terminal current with complex amplitude I, whose magnitude and phase is dependent on the complex permittivity of the material. The capacitive sensor 100 in one preferred embodiment has interdigitated electrodes as presented in U.S. Pat. Nos. 4,814,690 and 6,380,747, 6,486,673, and in U.S. patent application Ser. Nos. 10/040,797, filed Jan. 7, 2002, and 10/225,406, filed Aug. 20, 2002, the entire teachings of which are hereby incorporated by reference. This sensor 102 utilizes a pair of interdigitated electrodes 104 and 106 to produce a spatially periodic electric field. The electrodes are adjacent to the material of interest with an insulating substrate and a ground plane on the other side of the substrate. One of the two electrodes, 104, is driven with a sinusoidally varying voltage, VD, while the other, 106, is connected to a high-impedance buffer used to measure the magnitude and phase of the floating potential, vs. The periodicity of the electrode structure is denoted by the spatial wavelength $\lambda=2\pi/k$, where k is the wavenumber. Capacitive arrays with multiple sensing elements throughout the sensor footprint can also be used. For all of these sensors and sensor arrays, the response of each element must be measured with appropriate instrumentation. An example parallel architecture impedance measurement instrument is described in U.S. patent application Ser. No. 10/155,887, filed on May 23, 2002, the entire teachings of which are incorporated herein by reference.

An efficient method for converting the response of the MWM sensor into material or geometric properties is to use grid measurement methods. These methods convert the measured response from the sensor or sense element into the properties to be determined using a database of sensor response and provide for a real-time measurement capability. The database of responses is typically generated from a model for the sensor and the layered media proximate to the sensor. The measured response is often the transimpedance or transimpedance between the drive and sense element, which is typically a complex number. The magnitude and phase, or real and imaginary parts, of this complex number at each measurement frequency and/or each spatial wavelength excitation, are then used as inputs to the database. The measurement grids are two-dimensional databases that can be visualized as "grids" that relate two measured values to two unknown model parameters, such as the magnetic permeability (or electrical conductivity) and lift-off (where lift-off is defined as the proximity of the MUT to the plane of the MWM windings). For the characterization of coatings or surface layer properties, three- (or more)-dimensional versions of the measurement grids called lattices (or hypercubes) can be used. Alternatively, the surface layer parameters can be determined from numerical algorithms that minimize the least-squares error between the measurements and the predicted responses from the sensor, or by intelligent interpolation search methods within the grids, lattices or hypercubes. If the model accurately represents the geometric properties, such as the layers, of the test material then the properties obtained from these measurement grids are absolute properties. If the model does not accurately account for the aspects of the test material, such as the presence of individual layers or other spatial property variations, then the measurement grids provide effective or apparent properties that are associated with the test material and the sensor.

An advantage of the measurement grid method is that it allows for real-time measurements of the absolute electrical properties of the material and geometric parameters of interest. The database of the sensor responses can be generated prior to the data acquisition on the part itself, so that only table lookup and interpolation operations, which are relatively fast, needs to be performed. Furthermore, grids can be generated for the individual elements in an array so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations using standards and instrument preparation. The database could also include other properties or parameters of interest, such as the damage conditions or even the progression of these damage conditions, for rapid assessment and decision support purposes.

Figure 9:
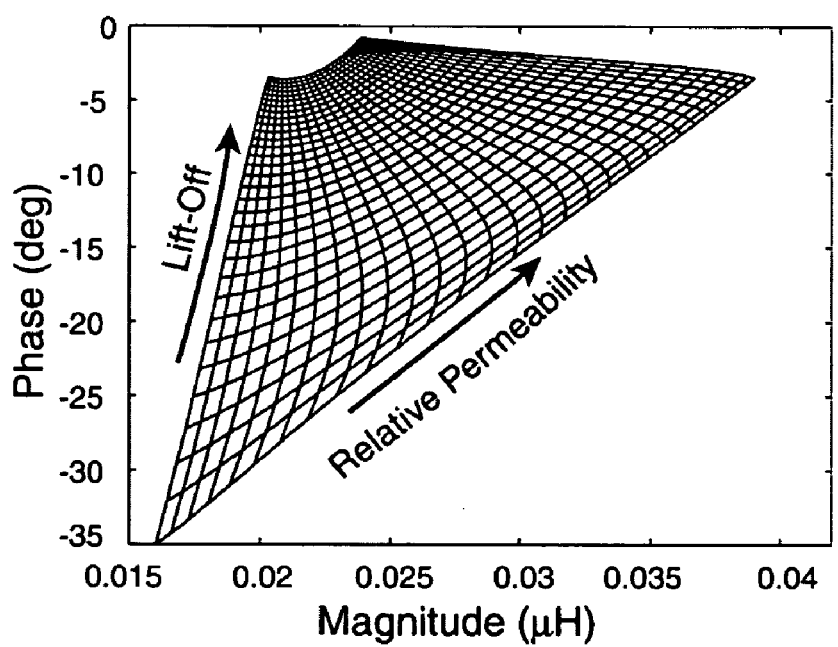
FIG. 9 illustrates a representative measurement grid relating the magnitude and phase of the sensor terminal impedance to the lift-off and magnetic permeability.
Figure 10:
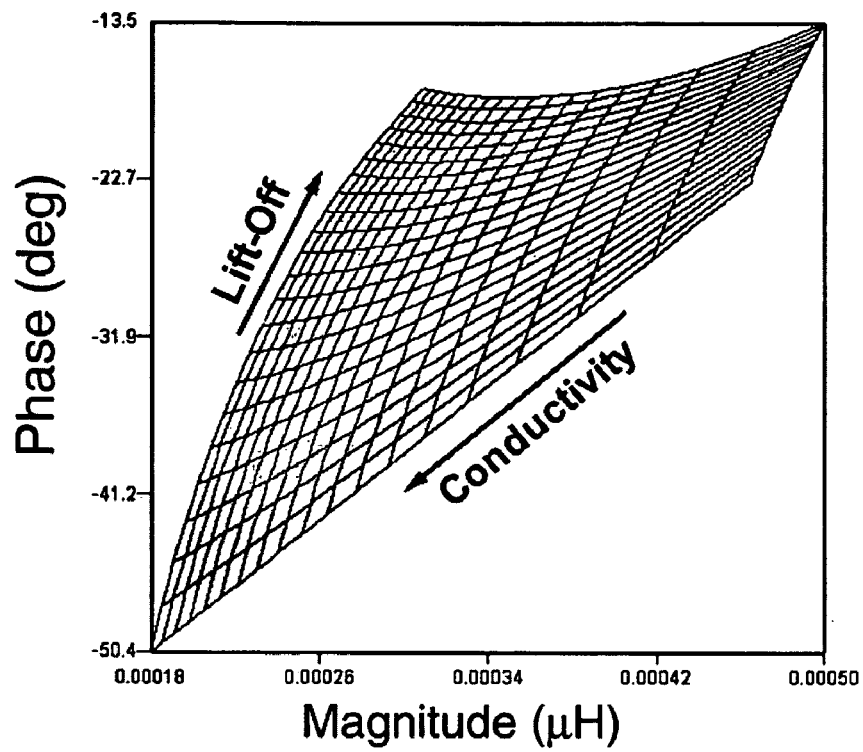
FIG. 10 illustrates a representative measurement grid relating the magnitude and phase of the sensor terminal impedance to the lift-off and electrical conductivity.

For ferromagnetic materials, such as most steels, a measurement grid provides conversion of raw data to magnetic permeability and lift-off. A representative measurement grid for ferromagnetic materials (e.g., carbon and alloy steels) is illustrated in FIG. 9. A representative measurement grid for a low-conductivity nonmagnetic alloy (e.g., titanium alloys, some superalloys, and austenitic stainless steels) is illustrated in FIG. 10. For coated materials, such as cadmium and cadmium alloys on steels, the properties of the coatings can be incorporated into the model response for the sensor so that the measurement grid accurately reflects, for example, the permeability variations of substrate material with stress and the lift-off. Lattices and hypercubes can be used to include variations in coating properties (thickness, conductivity, permeability), over the imaging region of interest.

Figure 11:
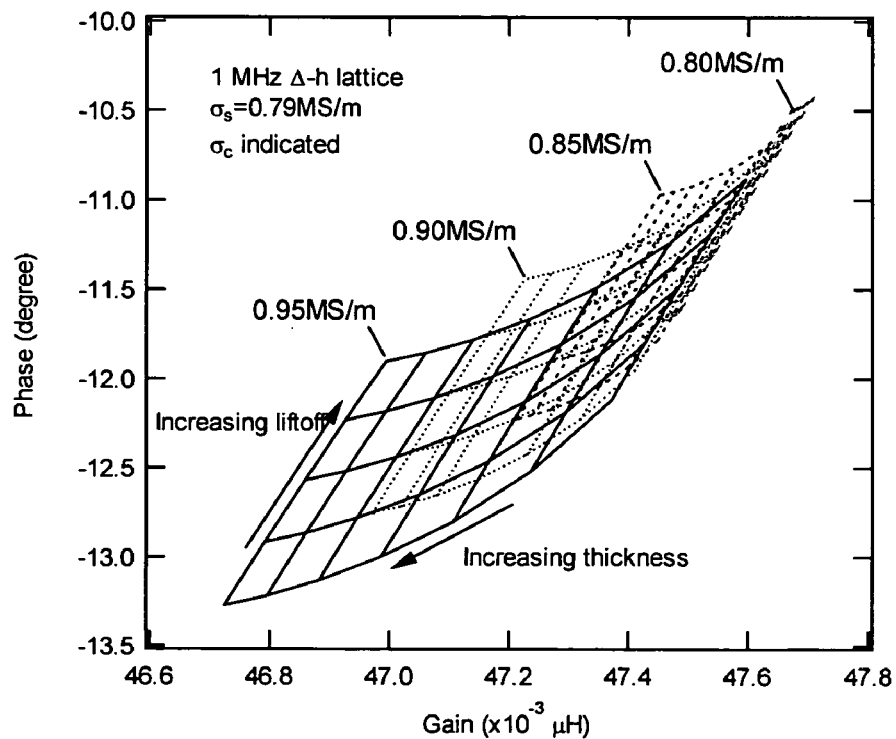
FIG. 11 illustrates a representative coating thickness/lift-off grid lattice for turbine blade materials.

The ability to measure several model parameters and correlate these to features of a metallic coating has been demonstrated. For example, multiple frequency eddy current measurements have been used for coating characterization and property profiling methods as described in U.S. Pat. No. 6,377,039 and ASTM Standard E2338-04, the entire contents of which are incorporated herein by reference. The multiple frequency coating characterization algorithm can be used to independently estimate three unknown material properties simultaneously by iteratively finding a set of parameter values that are constant over the frequency range. For a thermal barrier coating, these parameters are typically the coating conductivity, the coating thickness, and the lift-off or sensor proximity to the test material surface. In this algorithm, sensor responses for ranges of property variations are calculated and stored in databases. A measurement grid or a two-dimensional database of the sensor response is created in advance by varying the coating thickness, and lift-off over the range of interest for a given coating. In a lattice, measurement grids are created for a range of coating conductivities that span the range of interest for a given material, forming a three-dimensional database for the sensor response. A representative grid lattice for the characterization of turbine blade coatings is shown in FIG. 11. The lattice shows coating thickness-lift-off grids for four coating conductivities at a single frequency. In each measurement grid, the spacing between the grid points illustrates the sensitivity for independently estimating the coating thickness and the lift-off. The grid spacing and sensitivity is large when the coating and the substrate have significantly different conductivities; the grid collapses when the conductivities of the coating and the substrate are equal, which is expected for an uncoated specimen.

The coating characterization algorithm uses the measurement grid lattices to determine a set of coating properties that are independent of frequency. Alternatively, a non-linear least squares method can be used to minimize the error between the predicted response from a model for the property variations with depth and the measured data at multiple frequencies and/or multiple lift-offs. Computationally, the grid lattice approach, which only uses table look-ups and simple interpolations, tends to be faster than the non-linear least squares approach, which generally require multiple calculations from simulation model that can be complicated. Hybrid methods can improve the speed of the non-linear least squares approach and permit a real-time measurement capability by using precomputed grid lattices for the sensor responses in place of the calculations from the model.

Figure 12:
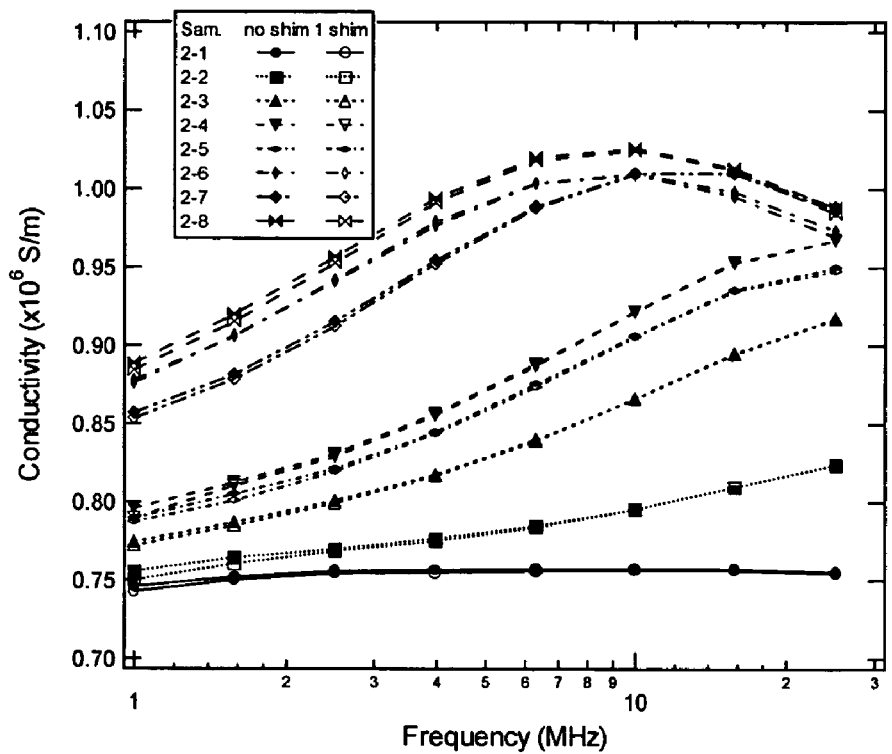
FIG. 12 is a plot of multiple frequency conductivity measurements for MCrAlY coatings on IN738 substrates obtained with a single element MWM.

A representative application of the three-parameter estimation algorithm is the determination of coating conductivity, coating thickness, and lift-off of a MCrAlY bond coat on an IN738 substrate. The effective conductivity is plotted against the frequency in FIG. 12. For the uncoated specimens, the conductivity is constant with frequency. For the coated specimens, the low-frequency response approaches the substrate conductivity as the skin depth of the magnetic field becomes large compared to the coating thickness. The high-frequency response approaches the coating conductivity as the skin depth of the magnetic field becomes small compared to the coating thickness. The data with a 0.001 in.

Figure 13:
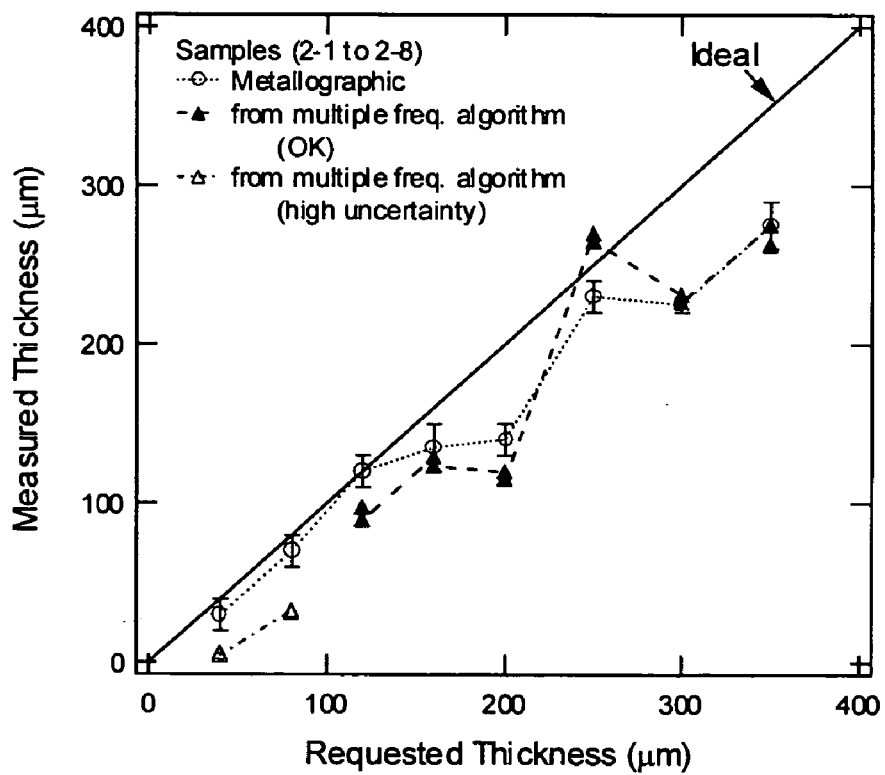
FIG. 13 illustrates a comparison between a coating thickness determined from the coating characterization algorithm, using the data of FIG. 12, and metallography.

(0.025 mm) thick shim placed between the sensor and the specimens yields exactly the same effective conductivity estimate as the data without a shim, which provides confidence in the quality of the calibration and the measurements. As shown in FIG. 13, there is good agreement with destructive metallographic measurements of the coating thickness for coatings thicknesses of 0.004 to 0.014 in. (0.100 to 0.350 mm).

Figure 14:
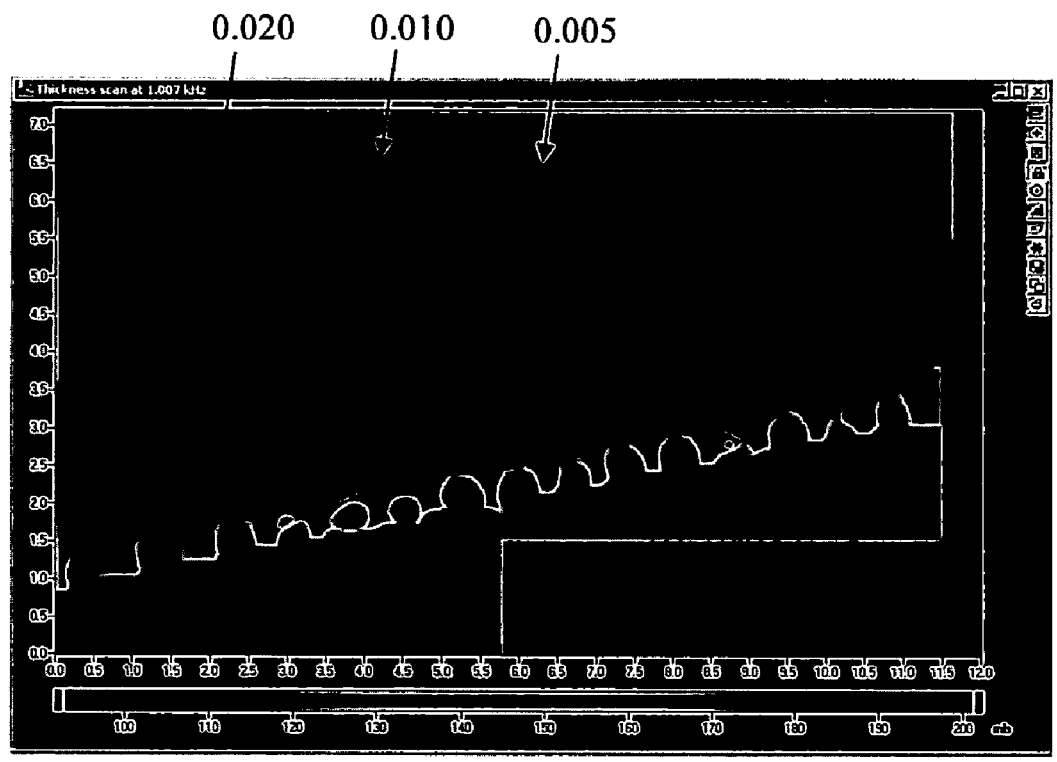
FIG. 14 is a representative scan image of wing plank remaining material thickness with milled out regions to simulate material loss.

Characterization of hidden features such as corrosion loss in material layers typically has trade-offs between the measurement or imaging speed and the accuracy or robustness of the feature assessment. Clearly, increasing the sensor translation scanning speed over a material allows coverage of more material in a given time period but can also reduce the spatial resolution of the data. Similarly, simplifying assumptions about the layer or material construct can reduce the number of unknown parameters or properties to be determined, at the potential expense of providing a poor assessment of the material condition. For a simple corrosion example where there is metal material loss in a single layer, the unknown parameters are typically the sensor lift-off (e.g., it can vary if the inspection is being performed through a paint layer), the electrical conductivity, and the thickness of the metal layer. Although this is generally a three unknown parameter problem, it is often possible to measure the electrical conductivity at a relatively high excitation frequency so that the measurement is not sensitive to the layer thickness. Then, assuming that the conductivity remains the same over the material, only two unknowns (thickness and lift-off) are need for the inspection. This then allows two-dimensional grid methods to be used, which are quite rapid. FIG. 14 shows an example image obtained from an inspection of a wing plank for hidden corrosion damage using such a two-dimensional measurement grid. Three regions were milled out in this wing plank to simulate corrosion loss of approximately 0.005, 0.010 and 0.020 in. (0.13, 0.25 and 0.51 mm) deep on the back side. The corresponding values for the maximum material loss depth estimate obtained with the hybrid sensor array for the milled out regions are 0.004, 0.011, and 0.022 in. (0.10, 0.28 and 0.56 mm), respectively, which are in good agreement with the actual depths measures with a depth gauge. The image also shows the basic thickness variations along different sections of the plank and semi-circular indications that correspond to fastener holes near the edge of the plank.

Figure 15:
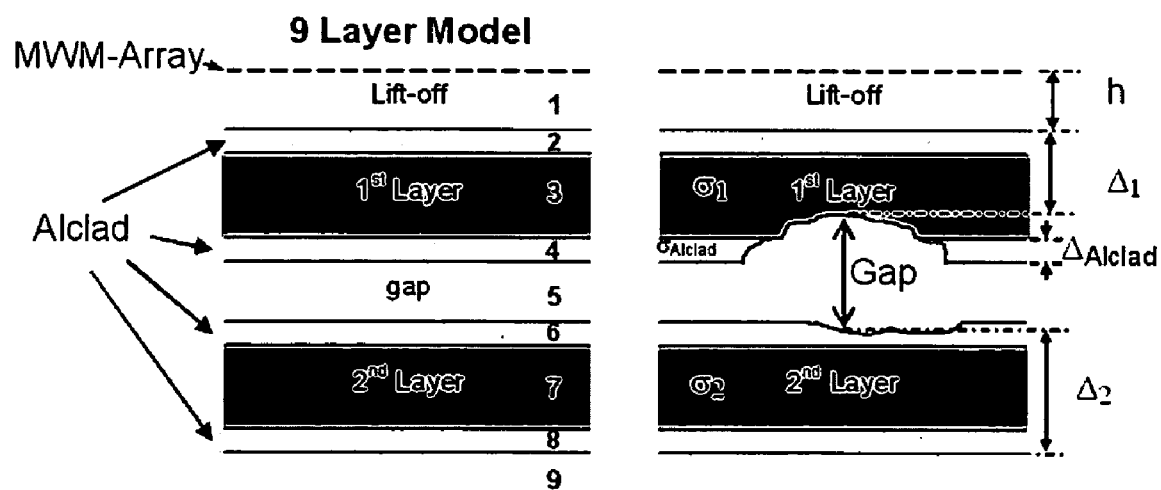
FIG. 15 illustrates a schematic of a multiple layered model.

In many other material systems, the characterization requires more than two unknown parameters. Again, for a corrosion example, consider the lap joint shown in FIG. 15. This figure shows a diagram of the nine-layer model appropriate for an aircraft lap joint, where aluminum cladding (Alclad) is used as a protective skin on each panel of the joint. One can typically get reasonable estimates of the electrical conductivities of the center sections of each panel, the nominal electrical conductivity of the Alclad, and the nominal thickness of the Alclad. Then, the remaining unknowns for measurement with an eddy current sensor are the lift-off, the thickness of each panel, and the gap thickness between each panel. When a doubler is included, another panel must be added to the model so that the model uses 13 layers instead of nine. Note that each of the Alclad layers must be accounted for since estimations that do not account for the Alclad layers can produce substantial errors in the material loss estimates. This is because the Alclad is nearly twice as conducting as the aluminum substrate material in each panel. Thus, a 0.002 in. (0.051 mm) thick Alclad layer on a 0.04 in. (1.02 mm) thick skin represents 5% of the thickness but not including it can result in errors as high as 5% of the thickness. Since the goal is often to estimate the thickness to within a few percent, not including the Alclad, alone, can make it impossible to achieve the required accuracy for material loss. If the eddy current sensor is calibrated on a standard that has different Alclad properties than the actual component under inspection, either in conductivity, thickness or both, then measurements on the actual component can have substantial errors in the estimated material loss.

Figure 16:
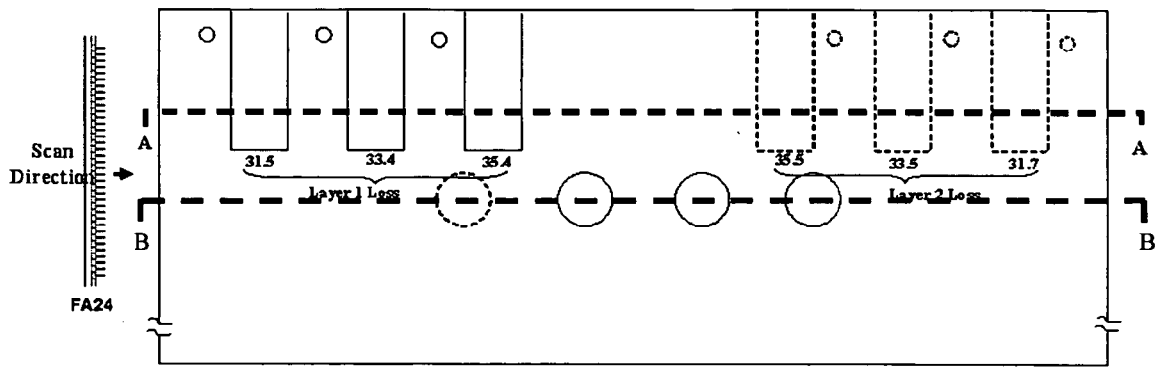
FIG. 16 illustrates a top view of a material loss calibration standard. The material loss dimensions are in 0.001 in. (0.0254 mm) increments.
Figure 17:
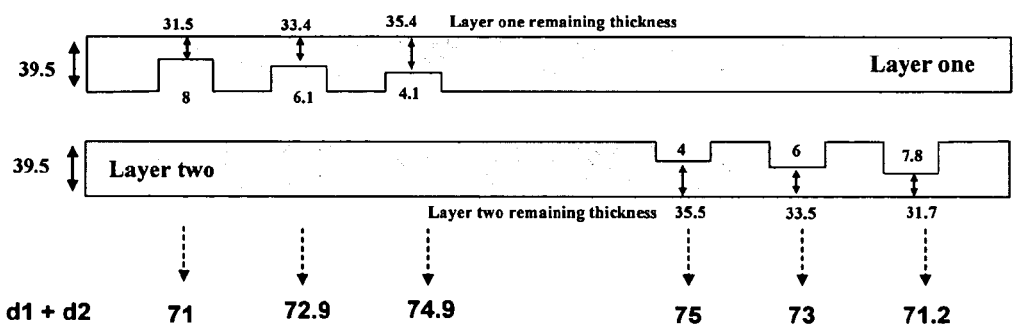
FIG. 17 illustrates the A—A cross-sectional view of the material loss calibration standard of FIG. 16. The material loss dimensions are in 0.001 in. (0.0254 mm) increments.
Figure 18:
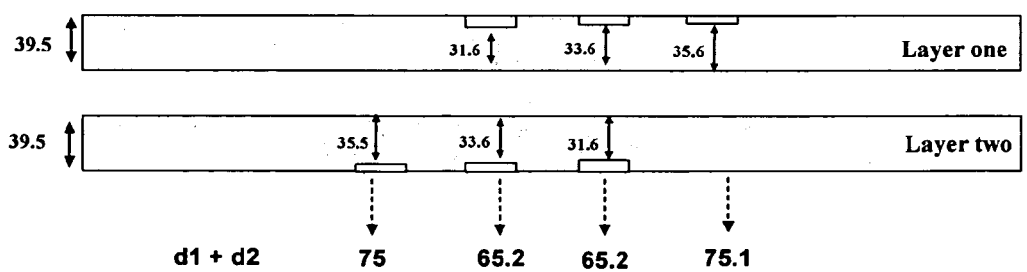
FIG. 18 illustrates the B—B cross-sectional view of the material loss calibration standard of FIG. 16. The material loss dimensions are in 0.001 in. (0.0254 mm) increments.
Figure 19:
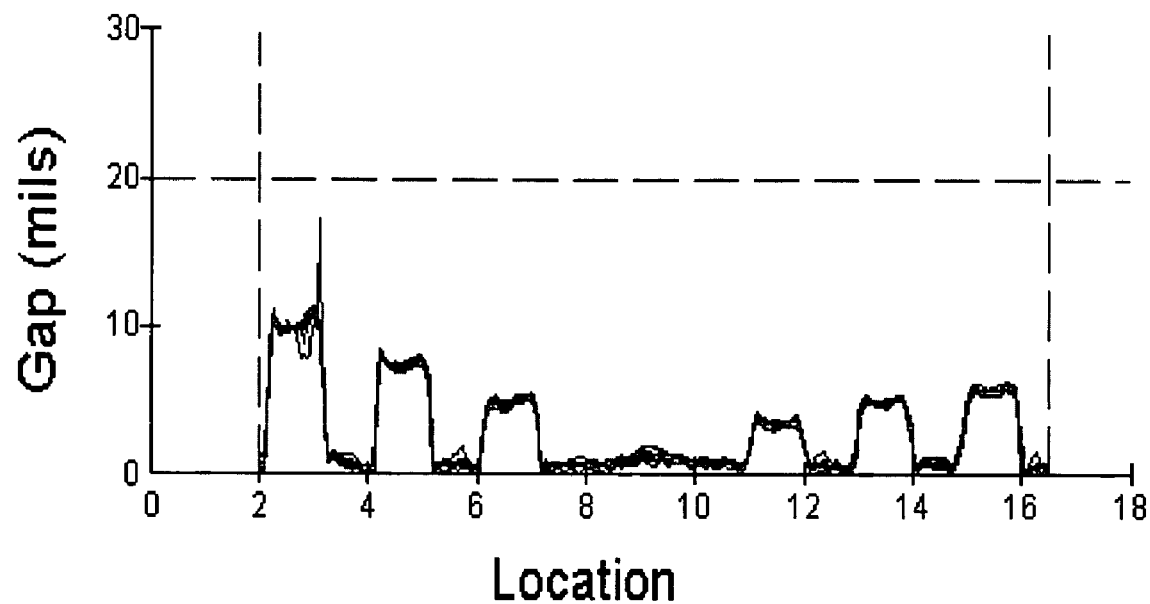
FIG. 19 illustrates the gap estimate for a three-unknown parameter method for the panel of FIG. 16 with no additional gap other than that created by the material loss regions.
Figure 20:
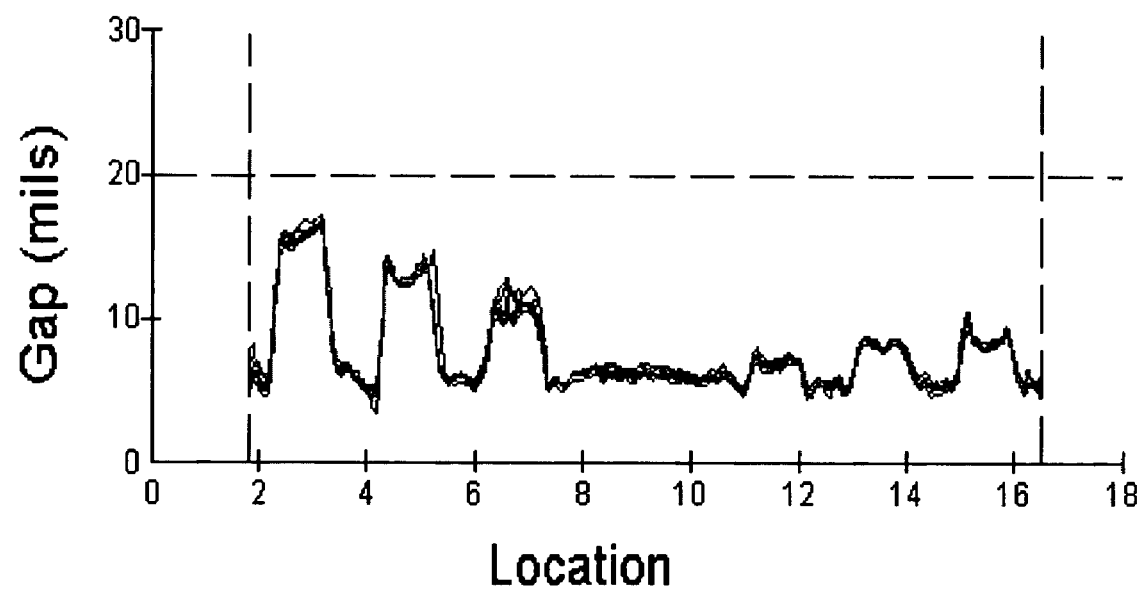
FIG. 20 illustrates the gap estimate for a three-unknown parameter method for the panel of FIG. 16 with a 0.005 in. (0.13 mm) shim between the material layers to simulate a uniform gap.

FIG. 16 shows a schematic for representative material loss calibration standard. This standard has rectangular areas and circular flat bottom holes milled out of each 0.0395 in. (1 mm) layer to various depths. This simulates material loss of varied severity and location (e.g., which material layer has the loss). The remaining thickness of each layer (denoted by d1 and d2 for layers 1 and 2, respectively) are indicated by the cross-sectional views of FIG. 17 for A—A and FIG. 18 for B—B. Note that the rectangular areas represent material loss at the interface between the two layers while the flat bottom holes represent material loss on the (visible) upper surface of layer 1 or the bottom surface of layer 2. Note that the rectangular regions are also similar to the shape of sealant grooves that are occasionally placed in joints between materials. An MWM-Array was scanned over the top of the sample, as indicated in FIG. 16 to create images of the estimated properties, such as the lift-off, gap thickness, and remaining material thickness, similar to FIG. 14. The response data from individual sense elements that passed over the simulated loss regions can also be plotted.

Multiple unknown or parameter estimation methods can be used to characterize material loss given, for example, by the sample in FIG. 16. An example three parameter method has the total thickness (layer 1 thickness plus the layer 2 thickness), the gap thickness (including material loss) and the lift-off (which can vary due to paint thickness variations, for example) being estimated. An example four parameter method has the first layer thickness, the second layer thickness, the gap thickness and the lift-off being estimated. In these examples, the thickness of each layer is used, instead of material loss itself, so that the nominal skin thickness is not required. Since corrosion tends to be localized, the nominal thickness in any critical region can often be established from the neighboring regions without requiring the operator to enter detailed information on each aircraft lap joint section. This is particularly valuable for tapered skin thicknesses. Additional known properties are the conductivity of the layers, which may be determined from other measurements on the layers themselves.

As described earlier, grid methods independently measure two unknown parameters, such as conductivity and lift-off, instead of simply compensating for lift-off variations. This is a substantial advantage over lift-off compensation methods typically employed with eddy current sensors. It accounts for nonlinear variations in the response (illustrated by the curvature of the grid lines). It also provides an absolute measurement of lift-off that can be used to determine the sensitivity, which is provided by the eigenvalues (or singular values when more measurements than unknowns are being considered) of the Jacobian matrix that relates the unknown vector to the measurement vector, which is approximated by the distances between the neighboring grid points divided by the incremental change in the unknown parameter at any location within the grid. The grid also provides a visual and computational tool for assessing performance that can reduce human errors and analysis of the data. It also provides a rapid method for inversion by permitting databases to be stored and used in real time to rapidly convert the measurement data into parameter estimate and create parameter or property images.

For more than two unknown parameters, measurement data from multiple operating conditions need to be combined so that there is a sufficient number of known values. For example, the transimpedance or transinductance is typically a complex number, having a real and imaginary part (or magnitude and phase), which provides two known values at a given excitation frequency. This allows two unknown parameters to be determined, since the number of known values equals the number of unknown parameters. Measurements can be performed at additional frequencies, so that the number of known values is greater than the number of unknown values, but this is an over-constrained situation where the extra measurements may provide some redundancy. For more than two unknown parameters, multiple excitation frequencies or multiple measurement conditions (e.g., sensors or sensor arrays that provide sensitivity to multiple spatial wavelengths or even multiple lift-offs) are needed. The various measurement conditions need to be sufficiently different so that the various unknown parameters can be estimated independently.

An example method for solving a multiple unknown parameter estimation problem is to use a common simplex method. This method starts with an initial set of candidate solutions and successively updates the candidate solution that has the largest error metric until the metric associated with each candidate solution is within a specified tolerance. The simplex algorithm tends to wander about the solution space moving from bad solutions toward, hopefully, the correct solution. This searching process tends to be relatively slow for multidimensional nonlinear spaces where responses vary gradually. Under such conditions, rate of change information can be used to reduce the solution time.

A faster multiple unknown parameter estimation method explicitly uses partial derivative information or the Jacobian. The Jacobian is a matrix of partial derivatives calculated at a particular point in the solution space. This Jacobian is precalculated and stored all of the database points. For example, one element of the Jacobian is the partial derivative of the real part of the first frequency's transinductance with respect to the lift-off. Using such derivative information enables large leaps from some original (presumably relatively poor) candidate solution to a better one, provided that the variation of the measured quantities with respect to the desired parameters is well described in the intervening region of the of the solution space by the Jacobian in effect at the original candidate solution. The use of Jacobians to identify optimal conditions using grids, lattice, and hypercubes was originally developed in U.S. Pat. No. 5,629,621 as a means for optimizing the operating conditions and geometry of an MWM-Array. Here, the methods are adapted to implement intelligent searching as a guide to the determination of multiple unknown parameters. This is particularly useful when massive amounts of data must be processed in real-time to generate images of the unknown parameters.

Figure 21:
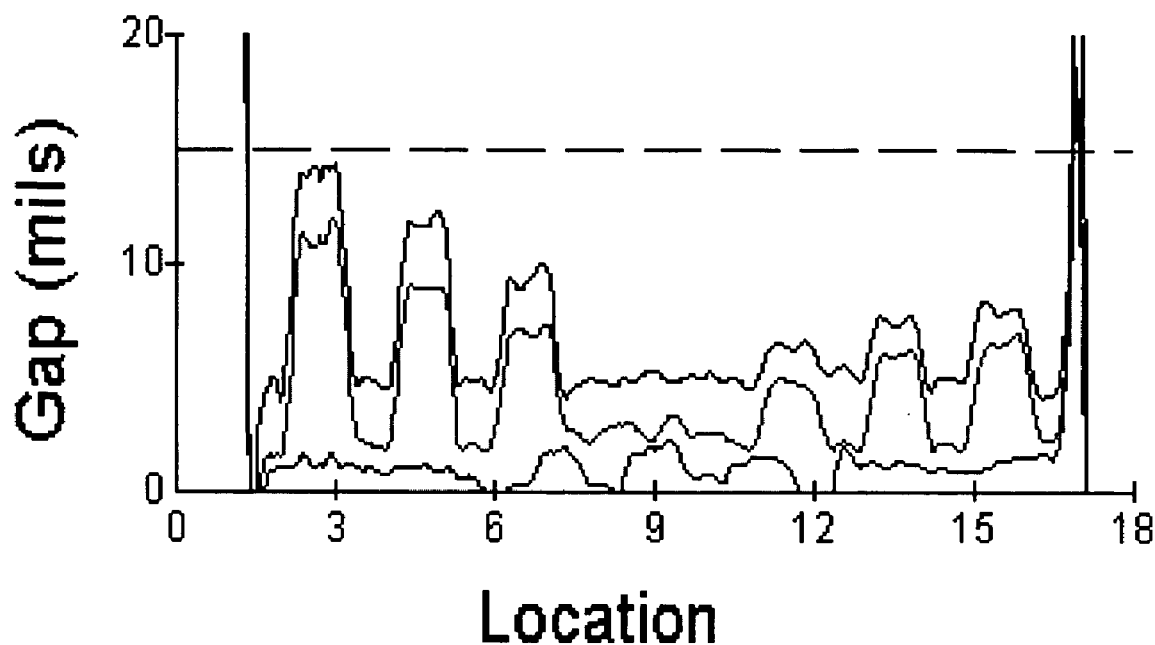
FIG. 21 illustrates the gap estimate for a three-unknown parameter method for the panel of FIG. 16 with a 0.005 in. (0.13 mm) shim between material layers along the upper 1 in. (25 mm) of the sample.
Figure 22:
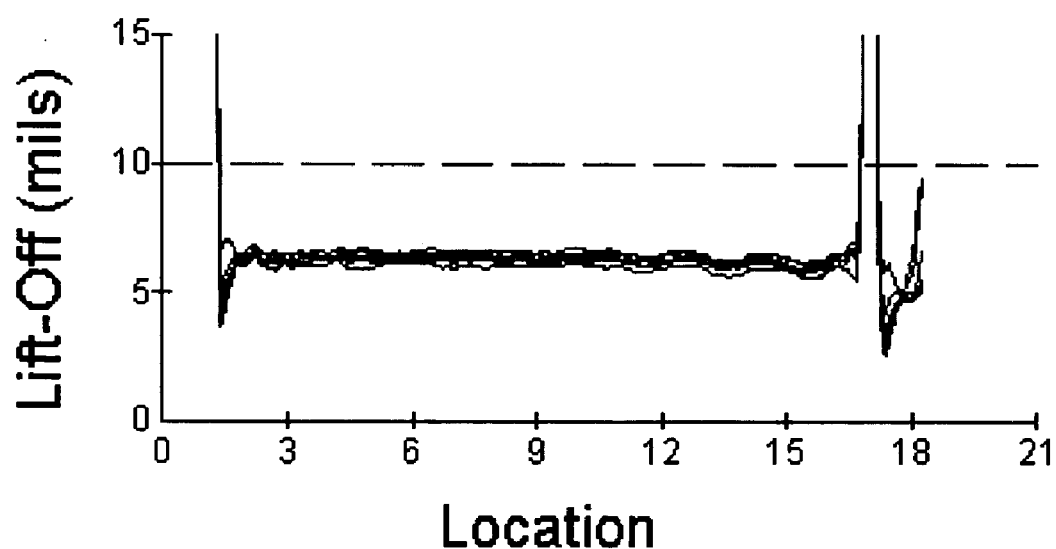
FIG. 22 illustrates lift-off estimates for the variable gap configuration of FIG. 21.
Figure 23:
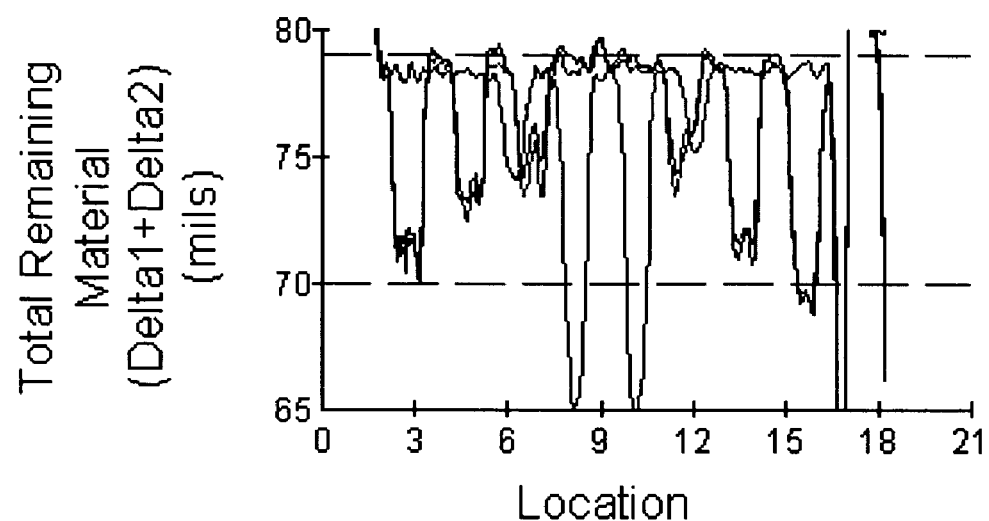
FIG. 23 illustrates total remaining material estimates for the variable gap configuration of FIG. 21.

Representative results for an application of the three-unknown parameter method is shown in FIGS. 19 through 23. In this case three excitation frequencies were used to estimate the total material loss, the gap and the lift-off (e.g., paint thickness), all independently at each data point within a scanned image to create C-scans. Only the results for selected sense elements or channels are plotted in the figures, which are B-Scans. The test panels were configured as shown earlier in FIG. 16, but with a few different gap conditions. The thickness of the material gap, shown for the rectangular loss regions, is accurately determined when the part is assembled as-is (FIG. 19), without any additional shims between the layers, when a 0.005 in. (0.127 mm) shim is placed between the material layers (FIG. 20) and when the 0.005 in. (0.127 mm) shim is only placed between a portion of the material layers (FIG. 21). This method also provides both the nominal gap thickness as well as the gap produced by the loss areas. Corresponding to the configuration of FIG. 21, FIG. 22 shows the lift-off being essentially constant across the sample, as expected for an unpainted clean part. Similarly FIG. 23 shows the total remaining material layer thicknesses, where the large reductions in thickness to approximately 0.065 in. (1.65 mm) at locations 8 and 10 correspond to the flat bottom holes. This illustrates the capability to independently measure total material loss and the actual gap, as well as the lift-off (or paint thickness). This was accomplished using an air calibration without the use of material loss or gap standards and assumed that the nominal Alclad thickness and layer conductivities were known. The accuracy of the method can be seen by comparing the specific areas to the dimensions provided in FIG. 16. For example, for the circular regions with loss both on the top exposed surface and the bottom exposed surfaces, the MWM-Array measured total thickness is approximately 0.065 in. (1.65 mm), which is within 0.0005 in. (0.013 mm) of the actual value. This level of accuracy appears to be achievable over a wide range of conditions with the MWM-Array and three unknown method. Similar results have also been obtained for both variable lift-off and variable gap conditions.

This same approach of scanning an MWM-Array over a test material and using a three unknown parameter analysis was applied to doubler configurations as well. Similar to FIG. 15, an additional material is placed on the bottom of the lap joint. This introduces unknowns for the Alclad layer thickness and conductivity, the bulk material thickness and conductivity, and the gap between the middle layer and the doubler. For this example, the estimated unknown parameters are still the total material thickness, the lift-off, and the gap between the upper two layers. Accounting for the gap variation in the lap joint as well as the doubler typically reduces the amount of material loss attributed to the corrosion and more accurately represents the remaining material thickness. Thus, in this case, not correcting for both the gap and the doubler could result in replacement of this lap joint, when it appears that the actual loss is far less severe than originally estimated.

The four-unknown parameter estimation approach was also applied to the independent estimation of the thicknesses of each layer along with the gap and the lift-off for the reference panel of FIG. 16. The value of independent layer thickness measurements is primarily to avoid nonconservative loss measurements. For example, if the loss is assumed to be on the second layer or equally on both layers and the actual loss is only on the second (deeper) layer, then two-unknown parameter estimation methods will tend to underestimate the loss. The three-unknown parameter estimation method total loss estimate reduces the potential for such nonconservative estimates, but is still not as good as independently estimating the thickness of each individual layer. The potential sensitivity for the independent measurement of different parameters can be visualized by plotting the measurement grids and looking at the size, shape, and spacing of the grid lines, as described above.

Representative results for an application of a four-unknown parameter method is shown in FIGS. 24 through 27.

Figure 24:
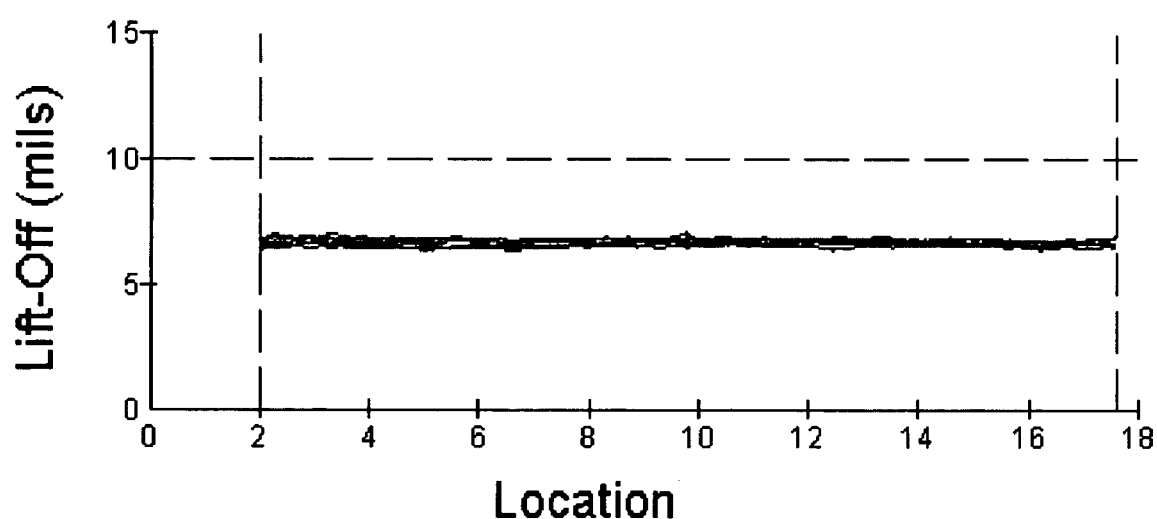
FIG. 24 illustrates the lift-off estimates for a four-unknown parameter method for the panel of FIG. 16.
Figure 25:
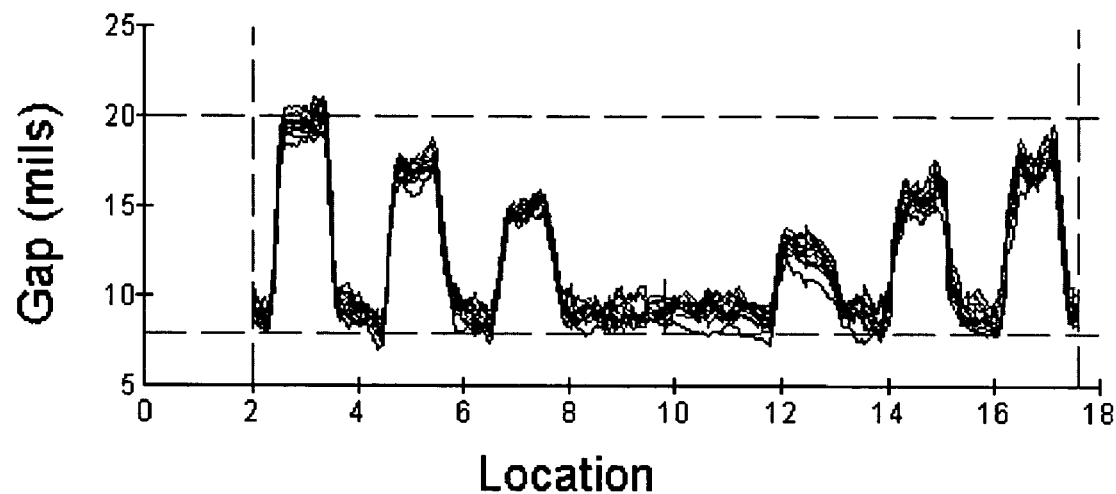
FIG. 25 illustrates the gap estimates corresponding to the data of FIG. 24.
Figure 26:
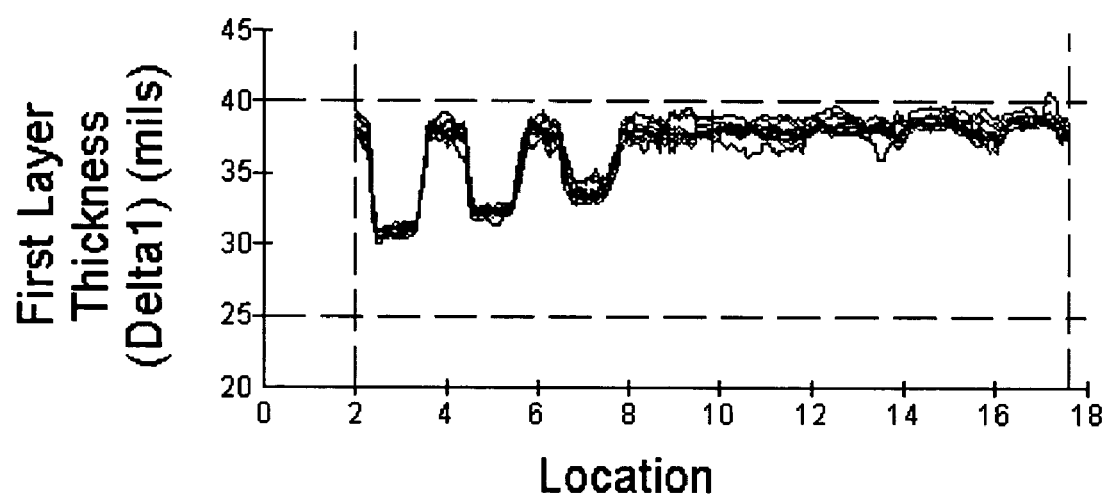
FIG. 26 illustrates the first layer thickness estimates corresponding to the data of FIG. 24.
Figure 27:
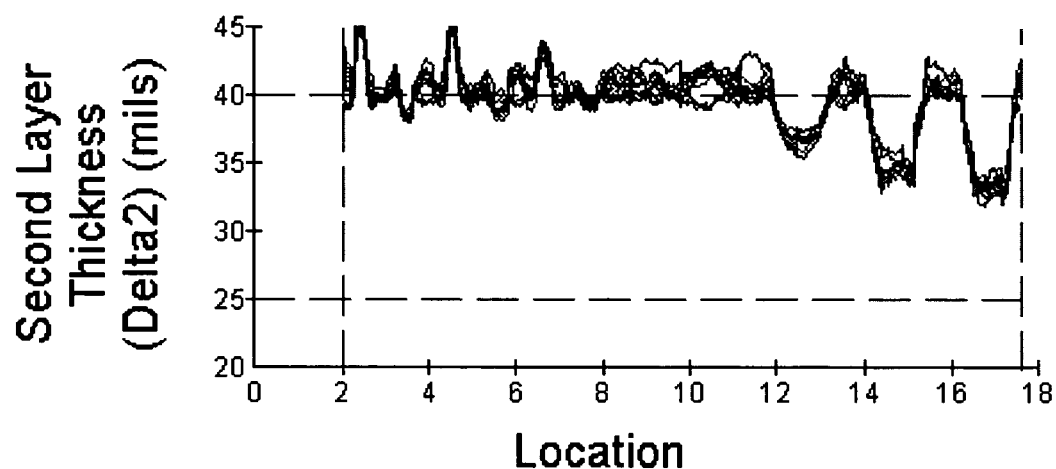
FIG. 27 illustrates the first layer thickness estimates corresponding to the data of FIG. 24.

In this case six excitation frequencies were used. Only the results for selected sense elements or channels that passed over the rectangular loss areas are plotted in the figures, but images of the responses over the entire material surface could also be displayed. FIG. 24 shows the lift-off, FIG. 25 shows the gap, FIG. 26 shows the first layer thickness, and FIG. 27 shows the second layer thickness. These estimates used known or assumed values for the conductivity of each layer along with the conductivity and thickness of the Alclad layers. No material loss standards were used in obtaining this data; the measurement data was converted to the unknown parameters, which also corresponded to the feature properties of interest (e.g., thicknesses) using only a reference calibration on two uniform panels with two different gaps and two different lift-offs. These figures demonstrate the capability to independently estimate the various model parameters (thicknesses) and to correlate them with the actual feature properties (thickness) of the reference panels. Thus, the method can correct for and estimate local gap and lift-off variations while independently measuring the first and second layer thicknesses.

Another hidden feature inspection application suitable for these model-based multiple unknown parameter estimation methods is the detection of near-surface hard alpha inclusions in titanium castings. These hard alpha inclusions can serve as initiation sites for fatigue cracks in cyclically loaded structures. As with any quasistatic method, the first step in selection of a measurement procedure is to determine the appropriate measurement configuration (sensor geometry and frequency) that would provide sensitivity to the defects of interest. For an eddy current sensor, this typically results in selecting a measurement frequency and sensor spatial wavelength. Note that lower frequencies and larger spatial wavelengths provide greater depth of penetration but lower frequencies tend to also have greater instrumentation noise; the measurement configuration has to balance these competing effects to find appropriate conditions for obtaining a depth of sensitivity of interest.

Figure 28:
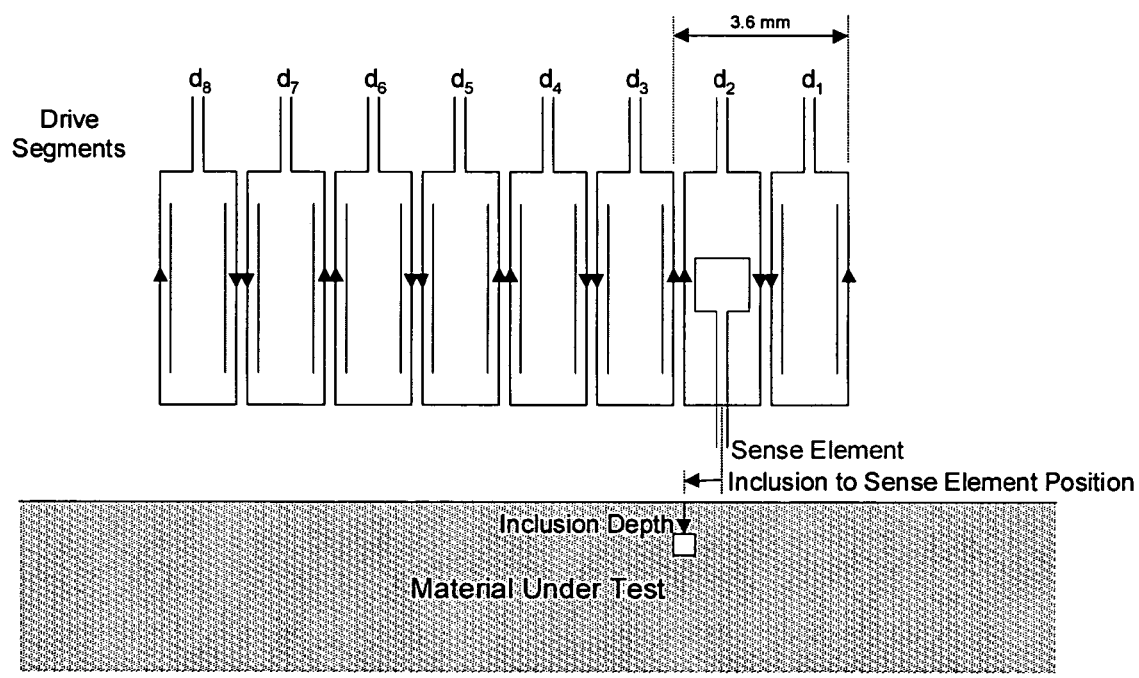
FIG. 28 illustrates a schematic view of an MWM sensor scanned over a square inclusion.

FIG. 28 shows a simplified geometry for an MWM sensor scanned over an inclusion. Unknown parameters for the inclusion include the lift-off, the electrical conductivity of the test material, and the size, depth, and conductivity of the inclusion itself. As with the lap joint configuration, the problem is simplified by assuming that that conductivity of the material under test and the inclusion are known. This then again reduces the parameter estimation problem to three unknowns.

Figure 29:
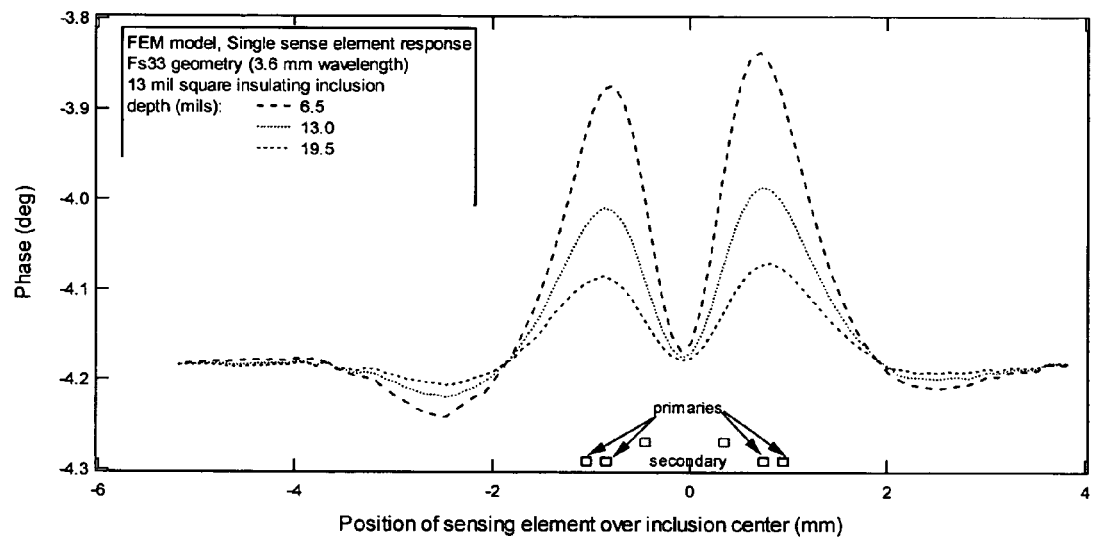
FIG. 29 illustrates simulated phase results for the geometry of FIG. 28 for a 0.0135 in. inclusion at several depths.

FIG. 29 shows the results of several numerical simulations as the sensor is scanned over an inclusion. The excitation frequency was 158 kHz and the phase of the response indicates that the response will show a double peak as the sensing element is scanned across an inclusion. This also shows the approximate position of the sense and drive windings nearest the sense winding when the inclusion is directly beneath the center of the sensing element. The peaks in the response occur when the inclusion is directly beneath the drive winding elements; this occurs as the currents induced in the test material are largest at these locations so that a lower conductivity inclusion interrupts the largest currents at these locations. These simulation results showing a double peak in the response have been verified by measurements on a Ti-64 alloy with artificial inclusions.

Figure 30:
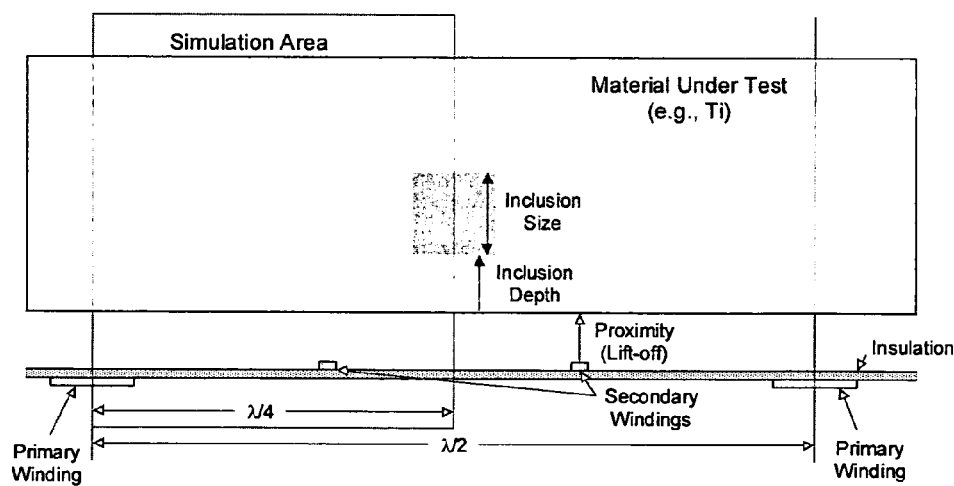
FIG. 30 illustrates the geometry for a numerical model for generating inclusion size and depth grids.
Figure 31:
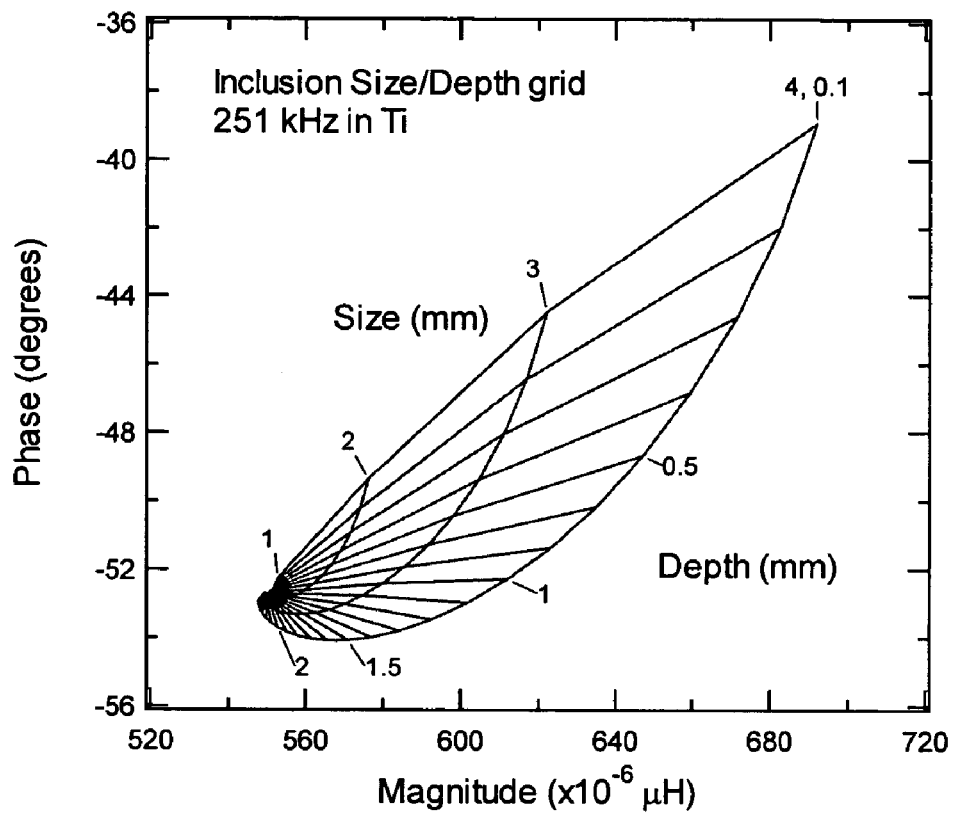
FIG. 31 illustrates a representative size-depth measurement grid.

As with the layered materials, grids and higher dimension databases can be generated to provide the real-time inversion of the measurement data into parameter estimates. As an example, FIG. 30 shows a schematic view of the geometry used to provide the size and depth of subsurface inclusions. Only a quarter wavelength of the sensor needed to be modeled due to symmetry. In this case, the inclusion was located at the center of the sensing elements. Although this is not the location of maximum measurement response, as indicated in FIG. 29, it was assumed that during a measurement scan it should be possible to determine when the secondary element is over the inclusion. The numerical model was used to determine the response of the sensor as the size and depth of the inclusion were varied, assuming that the conductivity of the material under test, the conductivity of the inclusion, and the proximity are known. A representative measurement grid is shown in FIG. 31 for an insulating inclusion in titanium at a frequency of 251 kHz. Larger inclusion sizes and shallower inclusion depths tend to cause a reduction in the phase response and an increase in the magnitude response of the sensor. Using information at a low frequency (for titanium), along with at least one other higher frequency that should provide information about the local conductivity and proximity, then allows the three and four unknown parameter estimation methods to be applied.

Figure 32:
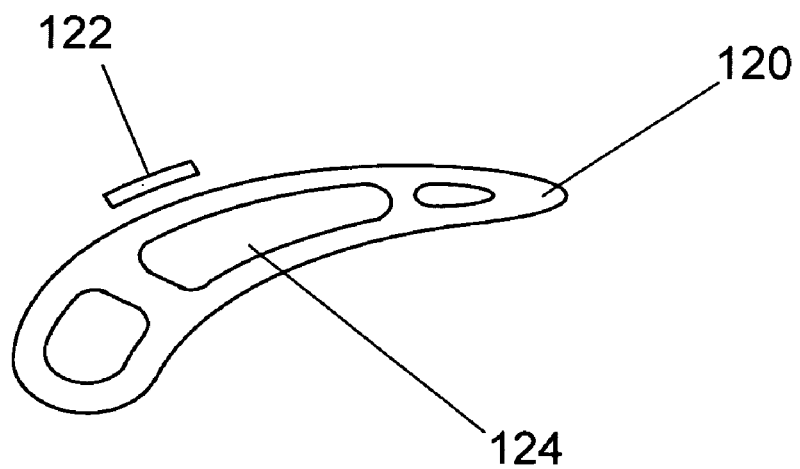
FIG. 32 illustrates a cross-sectional view of a turbine blade.

Similarly, these methods can also be applied to other geometries and applications. For example, FIG. 32 shows a cross-sectional view of a turbine blade 120 with coolant holes 122. Scanning the conformable sensor 124 over the surface allows the properties of the hidden coolant holes, the wall thickness, and even the wall itself to be measured. For metal turbine blades, this sensor could be an inductive or thermal sensor.

The MWM and MWM-Array sensors can also measure the permeability of a ferromagnetic substrate (steel) through a nonferromagnetic layer, i.e., an aluminum alloy coating. In this case the hidden feature is the ferromagnetic substrate and the property of interest is the stress variation of this substrate. Even without an applied load, the stress can vary due, among other factors, to the quality of the bond between the coating and the substrate. Differences in the residual stress can arise in areas where the coating is peeling away or has peeled away from the substrate. In a similar fashion, for the nonferromagnetic layer could be a cadmium coating on a steel landing gear component. These same methods would apply for monitoring the applied and residual stress (e.g., overload) conditions, as described for example in U.S. Provisional Application No. 60/505,197 filed Sep. 23, 2003, the entire teachings of which are incorporated herein by reference.

Figure 33:
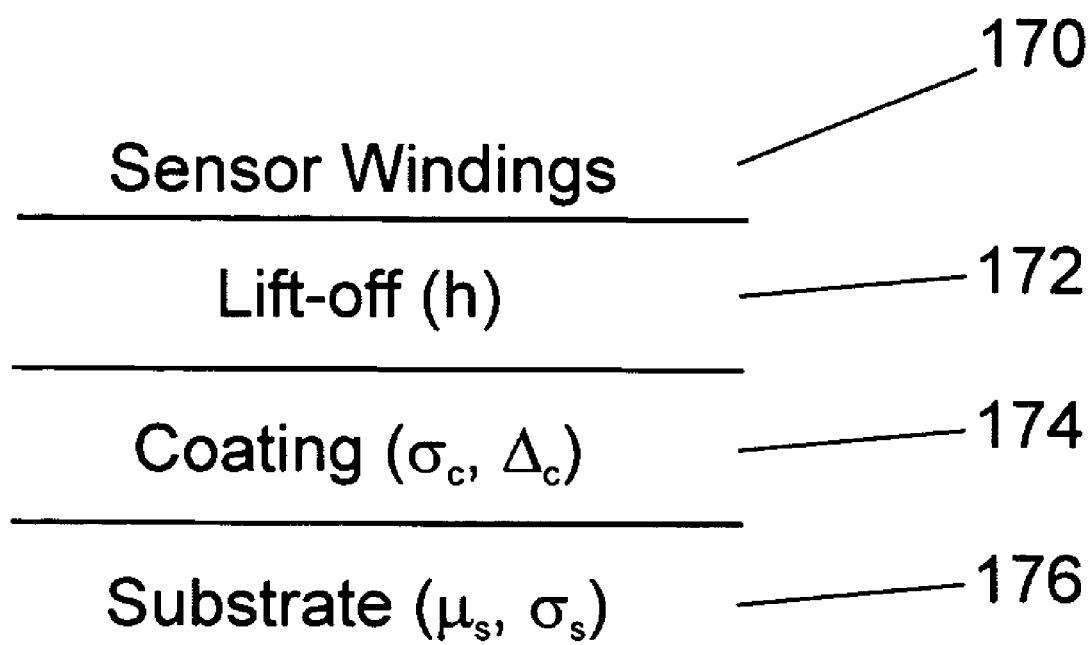
FIG. 33 illustrates a layered model for measurements on a ferromagnetic substrate with a nonferromagnetic coating.

In this example, FIG. 33 shows the representative layer geometry for the model. The test material itself has a conducting layer 174 on a magnetizable substrate 176. The sensor windings 170 are separated from the conductive coating by a lift-off layer 172. Typical unknown model parameters to be determined from the measurements are the lift-off (h), the coating conductivity ($\sigma_c$) and thickness ($\Delta_c$), and the substrate permeability ($\mu_c$). This allows variations in coating properties (such as porosity variations that affect the conductivity or even thickness variations from the coating process) to be accounted for, so that the estimates of the substrate permeability have minimal contamination from these other factors. Often, a nominal substrate conductivity is used in the model, since the substrate conductivity variation with stress is typically much smaller than the permeability variation with stress. Also, the coating may be magnetizable, but this introduces another unknown, which increases the time required for estimating the parameters and typically reduces the robustness of the estimate.

Measurements were performed on steel samples having an aluminum coating. An air calibration was used with an MWM so that reference panels were not used in the calibration. For the representative measurements described here, the sample had a nominal coating conductivity of 0.477% IACS, a coating thickness of 0.0148 in. (0.376 mm), and a substrate relative permeability of 68.8. Measurements were then performed with increasing nonconductive shim thicknesses between the sensor and the sample. The measured lift-off varied consistently with shim thickness over a range of 0.0015 to 0.0060 in. (0.038 to 0.15 mm) and was within 0.0001 in. (0.0025 mm) of the approximate shim thickness. Note that dust particles and pressure variations may cause variations on this order. The estimated parameters for the test material were essentially constant as the lift-off varied, with the coating conductivity variation less than 0.003% IACS, the coating thickness variation less than 0.0002 in. (0.005 mm) and the relative permeability variation less than 0.4. Scans were also performed with an MWM-Array at a scan rate of 1 in./sec that had been reference calibrated on a sample whose properties had been determined with an MWM. The sample was in its normal state so that the surface of the aluminum layer was convex. Additional scans were performed with the part pressed flaw. This resulted in applied compressive stresses in the steel substrate near the interface, which caused a reduction in the measured permeability of the steel at the aluminum-steel interface that was observed with the permeability images. Note that the aluminum coating thickness data did not vary with stress, demonstrating the independent measurement capability.

While the inventions have been particularly shown and described with reference to preferred embodiments thereof, it will be understood to those skilled in the art that various changes in form and details may be made therein without departing from the spirit and scope of the invention as defined by the appended claims.

References incorporated by reference in their entirety:

Haus, H. A. and Melcher, J. R. (1989), "Electromagnetic Fields and Energy," Prentice-Hall Inc., Englewood Cliffs, N.J.

The following references are also incorporated herein by reference in their entirety.

1. Air Force Phase II Final Report, titled "Detection and Imaging of Inclusion and Planar Flaws in Titanium Castings Including Weld Repaired Regions," Topic #AF00-162, dated Apr. 8, 2003.
2. Technical paper titled "Enhancements in MWM-Array Hidden Corrosion Imaging," JENTEK docket number TP_2003_0801.
3. Technical presentation titled "High-Resolution Residual Stress Imaging Using MWM-Arrays with Pre-Computed Response Databases," QNDE Conference, Colorado School of Mines, July 2004.

What is claimed is:

1. A method for characterizing a hidden feature in a test material, said method comprising:
   placing a sensor in proximity to the test material;
   measuring a quasistatic sensor response;
   providing a database that provides a model sensor response for a range of values for each of at least three model parameters; and
   using the database to convert the measured sensor response into the model parameters by selecting the model parameter values that correspond to the measured sensor response, at least one of the model parameters being quantitatively correlated to at least one property of the hidden feature of interest.

2. A method as claimed in claim 1 wherein the sensor is an electric field sensor.

3. A method as claimed in claim 1 wherein the sensor is a thermal field sensor.

4. A method as claimed in claim 1 wherein the sensor is a magnetic field sensor.

5. A method as claimed in claim 1 wherein the sensor comprises a drive element for imposing an interrogating field when driven by an electric signal and a sense element.

6. A method as claimed in claim 5 wherein the sensor further comprises multiple sensing elements.

7. A method as claimed in claim 6 wherein at least two of the multiple sensing elements are at different distances to the drive element.

8. A method as claimed in claim 1 wherein the feature is a corrosion loss.

9. A method as claimed in claim 8 wherein the at least one property is the thickness of at least one of:
   the test material and corrosion.

10. A method as claimed in claim 8 wherein the test material is a lap joint having at least two material layers.

11. A method as claimed in claim 10 wherein the at least one property is a gap thickness between layers of the lap joint.

12. A method as claimed in claim 10 wherein the at least one property is a thickness of a layer in the lap joint.

13. A method as claimed in claim 12 wherein another property is a thickness of a second layer in the lap joint.

14. A method as claimed in claim 8 where the test material has a cladding layer and the at least one model parameter is a thickness of the cladding layer.

15. A method as claimed in claim 1 wherein the feature is an inclusion.

16. A method as claimed in claim 15 wherein the at least one property is the inclusion depth.

17. A method as claimed in claim 15 wherein the at least one property is the inclusion size.

18. A method as claimed in claim 1 wherein the feature is local porosity.

19. A method as claimed in claim 1 wherein the feature is a sealant groove.

20. A method as claimed in claim 1 wherein the feature is a cooling hole in a turbine blade.

21. A method as claimed in claim 1 wherein the at least one parameter is an electrical conductivity.

22. A method as claimed in claim 1 wherein the at least one parameter is a magnetic permeability.

23. A method as claimed in claim 1 wherein the at least one parameter is sensor proximity to the test material.

24. A method as claimed in claim 1 wherein the test material has at least one layer and the at least one parameter is a layer thickness.

25. A method as claimed in claim 1 wherein the database further comprises rate of change of the sensor response with respect to changes in the model parameters.

26. A method as claimed in claim 1 wherein the at least one property is stress.

27. A method as claimed in claim 26 wherein the test material has a nonmagnetic conducting material layer on a magnetic material and the model accounts for a nonmagnetic conducting layer on a magnetic material.

28. A method as claimed in claim 1 wherein selecting the model parameter values uses interpolation.

29. A method as claimed in claim 1 wherein selecting the model parameter values uses a method that minimizes the difference between the model sensor response and measured sensor response.

* * * * *